(12) United States Patent
Wallace et al.

(10) Patent No.: US 12,151,042 B2
(45) Date of Patent: Nov. 26, 2024

(54) STERILIZATION SYSTEM AND METHOD

(71) Applicants: David Wallace, Mesa, AZ (US); John Patterson, Tempe, AZ (US); Nikhil Dave, Chandler, AZ (US); Abhik Chowdhury, Chandler, AZ (US); Katie Sue Pascavis, Gilbert, AZ (US)

(72) Inventors: David Wallace, Mesa, AZ (US); John Patterson, Tempe, AZ (US); Nikhil Dave, Chandler, AZ (US); Abhik Chowdhury, Chandler, AZ (US); Katie Sue Pascavis, Gilbert, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 26 days.

(21) Appl. No.: 17/243,336

(22) Filed: Apr. 28, 2021

(65) Prior Publication Data
US 2021/0338869 A1  Nov. 4, 2021

Related U.S. Application Data

(60) Provisional application No. 63/018,376, filed on Apr. 30, 2020.

(51) Int. Cl.
*A61L 2/20* (2006.01)
*A61L 2/24* (2006.01)
(Continued)

(52) U.S. Cl.
CPC ............... *A61L 2/202* (2013.01); *A61L 2/24* (2013.01); *C01B 13/115* (2013.01);
(Continued)

(58) Field of Classification Search
CPC ........ A61L 2/202; A61L 2/24; A61L 2101/02; A61L 2202/11; A61L 2202/14;
(Continued)

(56) References Cited

U.S. PATENT DOCUMENTS

| 3,801,791 A | 4/1974 | Schaefer |
| 4,818,498 A | 4/1989 | Bachhofer et al. |

(Continued)

FOREIGN PATENT DOCUMENTS

| CN | 108796542 A | * | 11/2018 | ............... C25B 1/13 |
| JP | 10120404 A | * | 5/1998 | |
| KR | 100462505 B1 | * | 12/2004 | |

OTHER PUBLICATIONS

3M., "Technical Bulletin Surgical N95 vs. Standard N95—Which to Consider?" Mar. 2020, Revision 2.

(Continued)

*Primary Examiner* — Xiuyu Tai
(74) *Attorney, Agent, or Firm* — Michael Best & Friedrich LLP

(57) ABSTRACT

A sterilization system includes a controller, a transformer including a primary side in communication with the controller and secondary side, an ozone generator in communication with the secondary side of the transformer and the controller, and a power source in communication with the controller, wherein the ozone generator ionizes atmospheric oxygen through the application of corona discharge.

17 Claims, 15 Drawing Sheets

(51) Int. Cl.
  *C01B 13/11* (2006.01)
  *A61L 101/02* (2006.01)
(52) U.S. Cl.
  CPC ........ *A61L 2101/02* (2020.08); *A61L 2202/11* (2013.01); *A61L 2202/14* (2013.01); *A61L 2202/24* (2013.01); *C01B 2201/22* (2013.01); *C01B 2201/62* (2013.01); *C01B 2201/90* (2013.01)
(58) Field of Classification Search
  CPC ........ A61L 2202/24; A61L 9/20; A61L 9/015; C01B 2201/22; C01B 2201/62; C01B 2201/90; C01B 13/115; C01B 2201/14; C01B 13/11; C01B 13/10; C01B 2201/82; B01J 19/08; B01J 19/088; B01J 19/087; B01J 2219/0871; B01J 2219/0841; B01J 2219/0809; B01J 2219/0828; B01J 2219/0833; B01D 53/38; B01D 2257/504; B01D 2257/91; B01D 2259/4558; B01D 2253/102; B01D 2259/804; B01D 2259/4541; B01D 2251/104; B01D 2259/4566; B01D 53/86; B01D 2259/4583; A62B 23/00; A62B 17/04; A62B 17/006; Y02P 20/151
  See application file for complete search history.

(56) References Cited

U.S. PATENT DOCUMENTS

| | | | |
|---|---|---|---|
| 5,516,493 A * | 5/1996 | Bell ........................ | C01B 13/11 422/907 |
| 5,520,893 A * | 5/1996 | Kasting, Jr. ............. | A61L 2/202 422/301 |
| 5,871,701 A | 2/1999 | Long | |
| 6,019,949 A * | 2/2000 | Dunder ................. | C01B 13/115 422/186.07 |
| 6,482,369 B2 | 11/2002 | Wang | |
| 7,077,890 B2 | 7/2006 | Botvinnik | |
| 7,658,891 B1 * | 2/2010 | Barnes .................... | C01B 13/11 128/205.28 |
| 2002/0058000 A1* | 5/2002 | Smith ................... | C01B 13/115 204/176 |
| 2005/0186108 A1* | 8/2005 | Fields ..................... | A61L 2/202 422/123 |
| 2007/0071658 A1 | 3/2007 | Kasten | |
| 2011/0318238 A1* | 12/2011 | Chen ...................... | B01J 19/087 422/186.18 |
| 2017/0335470 A1* | 11/2017 | Gykiere ................. | A23B 7/152 |
| 2017/0370013 A1* | 12/2017 | Bahar ..................... | C25B 15/02 |

OTHER PUBLICATIONS

Bahl, P., Doolan, C., de Silva, C., Chughtai, A., Bourouiba, L., MacIntyre, C. (2020). Airborne or droplet precautions for health workers treating COVID-19? Oxford University Press for the Infectious Diseases Society of America.
Batakliev, T., Georgiev, V., Anachkov, M., Rakovsky, S., Zaikov, G.E., Interdisciplinary Toxicology, 2014, vol. 7(2):47-59, Ozone Decomposition.
Battelle. (2016). Final Report for the Bioquell Hydrogen Peroxide Vapor (HPV) Decontamination for Reuse of N95 Respirators.
CDC, "Recommended Guidance for Extended Use and Limited Reuse of N95 Filtering Facepiece Respirators in Healthcare Settings," (Mar. 2020). Centers for Disease Control and Prevention.
Centers for Disease Control and Prevention. (Mar. 14, 2020). Personal Protective Equipment: Questions and Answers.
Chin, A., Chu, J., Perera, M., Hui, K., Yen, H., . . . Poon, L. (May 1, 2020). Stability of SARS-CoV-2 in different environmental conditions. The Lancet Microbe, vol. 1, Issue 1, e10.
Dry & Dry, "Premium Silica Gel Blue Indicating(Blue to Pink) Silica Gel Beads Desiccant Beads(Industry Standard 2-4 mm)—Rechargeable(7.5 LBS) Moisture Absorber Silica Gel," <https://www.amazon.com/dp/B013L2Z2MY/ref=redir_mobile_desktop?_encoding=UTF8&psc=1&ref=ppx_pop_mob_b_asin_title> date first available Aug. 7, 2015.
Fairfax, R., Lopez, L., Paulsen, L., Kilens, G. (2011). OSHA Compliance Issues The Assessment of Worker Exposure to Ozone during Manual and Automatic Spring Water Bottling. Journal of Applied Occupational and Environmental Hygeine.
Grossman, J., Pierce, A., Mody, J., Gagne, J., Sykora, C. Sayood, S., . . . Eckhouse, S. (Apr. 22, 2020). Institution of a Novel Process for N95 Respirator Disinfection with Vaporized Hydrogen Peroxide in the setting of the COVID-19 Pandemic at a Large Academic Medical Center. Journal of the American College of Surgeons.
Guo Z-D, Wang Z-Y, Zhang S-F, Li X, Li L, Li C., . . . Chen, W. (Apr. 10, 2020). Aerosol and surface distribution of severe acute respiratory syndrome coronavirus 2 in hospital wards, Wuhan, China, 2020. Emerg Infect Dis.
Hiroshi, T., Sakurai, M., Kousuke, I., Yoshiaki, M. (2009). Inactivation of Influenza Virus by Ozone Gas. IHI Engineering Review. vol. 42 No. 2., pp. 108-111.
Kenney, P., Chan, B., Kortright, K., Cintron, M., Havill, N., Russi, M., . . . Martinello, R. (2020). Hydrogen Peroxide Vapor sterilization of N95 respirators for reuse . MedRxiv.
Kogelschatz, U., Eliasson, B., Hirth, M. (1988). Ozone Generation from Oxygen and Air: Discharge Physics and Reaction Mechanisms. The Journal of the International Ozone Association.
Lam, "Ozone Disinfection of SARS-Contaminated Areas," Enviro Labs Limited, Apr. 2020.
Lindsley, W., Martin, S., Thewlis, R., Sarkisian, K., Nwoko, J., . . . Noti, J. (Aug. 2015). Effects of Ultraviolet Germicidal Irradiation (UVGI) on N95 Respirator Filtration Performance and Structural Integrity. Journal of Occupational and Environmental Hygiene.
Maier, I., Chu, T. (2016). Use of Ozone for Inactivation of Bacteria and Viruses in Cryostats. Journal of Cytology and Histology.
Miles, J. (1994). Occupational Safety and Health Administration's (OSHA) regulations for ozone. United States Department of Labor.
Niosh. Guide to the Selection and Use of Particulate Respirators. (2014). CDC.
Niosh. (2019). Determination of particulate filter efficiency level for N95 series filters against solid particulates for non-powdered, air-purifying respirators, Standard Testing Procedure (STP), TEB-APR-STP-0059, 2019.
Niosh. (2019). Determination of particulate filter efficiency level for P99 series filters against liquid particulates for non-powdered, air-purifying respirators, Standard Testing Procedure (STP), TEB-APR-STP-0052, 2019.
Parts Galaxy Store, "Set of 6 Ignition Coils for Various Ford Mazda Mercury 3.0L V6 fits DG-500 / DG500 / FD502," <https://www.amazon.com/gp/product/B01EGS5IG2/ref=ppx_yo_dt_b_search_asin_title?ie=UTF8&psc=1> date first available Apr. 18, 2016.
Prather, K., Wang, C., Schooley, R. (2020). Reducing transmission of SARS-CoV-2. Science.
Rutala, W. A., & Weber, D. J. (2015). Disinfection, Sterilization, and Control of Hospital Waste. Mandell, Douglas, and Bennett's Principles and Practice of Infectious Diseases, 3294-3309.e4.
Sain Smart, "MQ-131 Gas Sensor Ozone Module," <https://www.sainsmart.com/products/mq-131-gas-sensor-ozone-module?variant=126446534676&currency=USDS$gclid=EAlalQobChMlgKCUzd-6AlVjsJkCh0wbgJvEAQYAi> available at least as early as Apr. 18, 2020.
Sanche S, Lin YT, Xu C, Romero-Severson E, Hengartner N, Ke R. (2020). High contagiousness and rapid spread of severe acute respiratory syndrome coronavirus 2. Emerg Infect Dis.
Shah, S. and Bhargava, A. (Oct. 2017). Recent advances in low temperature sterilization—Moving ahead from Cidex (TM)/ETO to OPA/Ozone: An update. Indian Journal of Anesthesia.
Speed, D., Westerhoff, P., Sierra-Alvarez, R., Draper, R., Pantano, P., Aravamudhan, S., . . . Shadman, F. (2015). Physical, chemical, and in vitro toxicological characterization of nanoparticles in chemical mechanical planarization suspensions used in the semiconductor

(56) References Cited

OTHER PUBLICATIONS industry: Towards environmental health and safety assessments. Environmental Science: Nano, 2, 227-244.

Technical Committee ISO/TC 198. (2017). I SO/TS 19930:2017(en) Guidance on aspects of a risk-based approach to assuring sterility of terminally sterilized, single-use health care product that is unable to withstand processing to achieve maximally a sterility assurance level of 10-6. ISO Online Browsing Platform.

Van Doremalen, N., Bushmaker, T., Morris, D., Holbrook, M., Gamble, A., Williamson, B., . . . Munster, V. (Apr. 16, 2020). Aerosol and Surface Stability of SARS-CoV-2 as Compared with SARS-CoV-1. The New England Journal of Medicine.

World Health Organization. (2020). Coronavirus disease (COVID-19) situation reports, https://www.who.int/emergencies/diseases/novel-coronavirus-2019/situation-reports.

* cited by examiner

STERILIZATION SYSTEM AND METHOD

CROSS-REFERENCE TO RELATED APPLICATIONS

This application is a non-provisional of and claims the benefit of U.S. Patent Application No. 63/018,376, filed on Apr. 30, 2020, the contents of which are incorporated herein by reference.

FIELD

The present disclosure relates to a sterilization system, and in particular, to a sterilization system for industrial, medical, consumer, or other applications.

BACKGROUND

Severe acute respiratory syndrome coronavirus 2 (SARS-COV-2), an elusive and highly pathogenic agent, has resulted in the ongoing COVID-19 pandemic affecting numerous populations worldwide. New studies investigating the tenacity of SARS-COV-2 have highlighted its ability to persist on a myriad of surfaces for several days, including gowns and shoes. As a result, there is a global need for sterilization of a variety of potentially-contaminated items, ranging from clothing to personal protective equipment, like face coverings, to consumer goods (e.g., electronic devices, office supplies, etc.). Accordingly, there is a need for a cost-effective, scalable, and sustainable sterilization system.

SUMMARY

In another construction, a sterilization system or an ozone generation system is provided including a low-cost modular ozone generator that generates ozone from atmospheric air. In one construction, the sterilization system provides a reliable and consistent source of ozone gas using widely-available and cost-effective materials that is modular and scalable in its applications.

The ozone may be used in industrial, medical, consumer, or other applications. That is, the system pertains to any suitable use case where ozone gas is required to be generated from atmospheric air or another oxygen-rich gas supply. In particular, the disinfection and sterilization of medical supplies or personal protective equipment such as masks, re-usable medical equipment, and clothing is one suggested use case for the invention disclosed herein.

The system includes silicone-insulated conductors arranged in such a way to promote corona discharge without inducing dielectric breakdown in their insulation. The combination of this unique electrode configuration with a suitable high-voltage power source enables the production of ozone in suitable quantity for use as a disinfectant.

In one construction, a sterilization system includes a controller, a transformer including a primary side in communication with the controller and secondary side, an ozone generator in communication with the secondary side of the transformer and the controller, and a power source in communication with the controller, wherein the ozone generator ionizes atmospheric oxygen through the application of corona discharge.

In another construction, the sterilization system includes a chassis, a controller positioned within the chassis, a transformer positioned within the chassis and including a primary side in communication with the controller and secondary side, an ozone generator positioned within the chassis and in communication with the secondary side of the transformer and the controller, a power source positioned within the chassis and in communication with the controller, and a fan mounted to the chassis and in communication with the controller, the fan configured to circulate air across the ozone generator, wherein the ozone generator ionizes of atmospheric oxygen through the application of corona discharge.

In another construction, the sterilization system includes a chassis, a controller positioned within the chassis and an ignition coil including a primary side in communication with the controller and secondary side. A first electrode and a second electrode are twisted together. The first and second electrodes are in communication with the secondary side of the transformer and the controller. A power source is positioned in communication with the controller, and a fan is in communication with the controller. The fan is configured to circulate air across the ozone generator. The first and second electrodes ionize atmospheric oxygen through an application of corona discharge.

In yet another construction, a method of assembling a sterilization system includes forming an ozone generator and coupling the ozone generator to a power source.

In yet another construction, a method of use of a sterilization system includes generating ozone by guiding air over an ozone generator, and sterilizing a material or space positioned adjacent the ozone generator.

Other aspects of the disclosure will become apparent by consideration of the detailed description and accompanying drawings.

DETAILED DESCRIPTION

Figure 1:
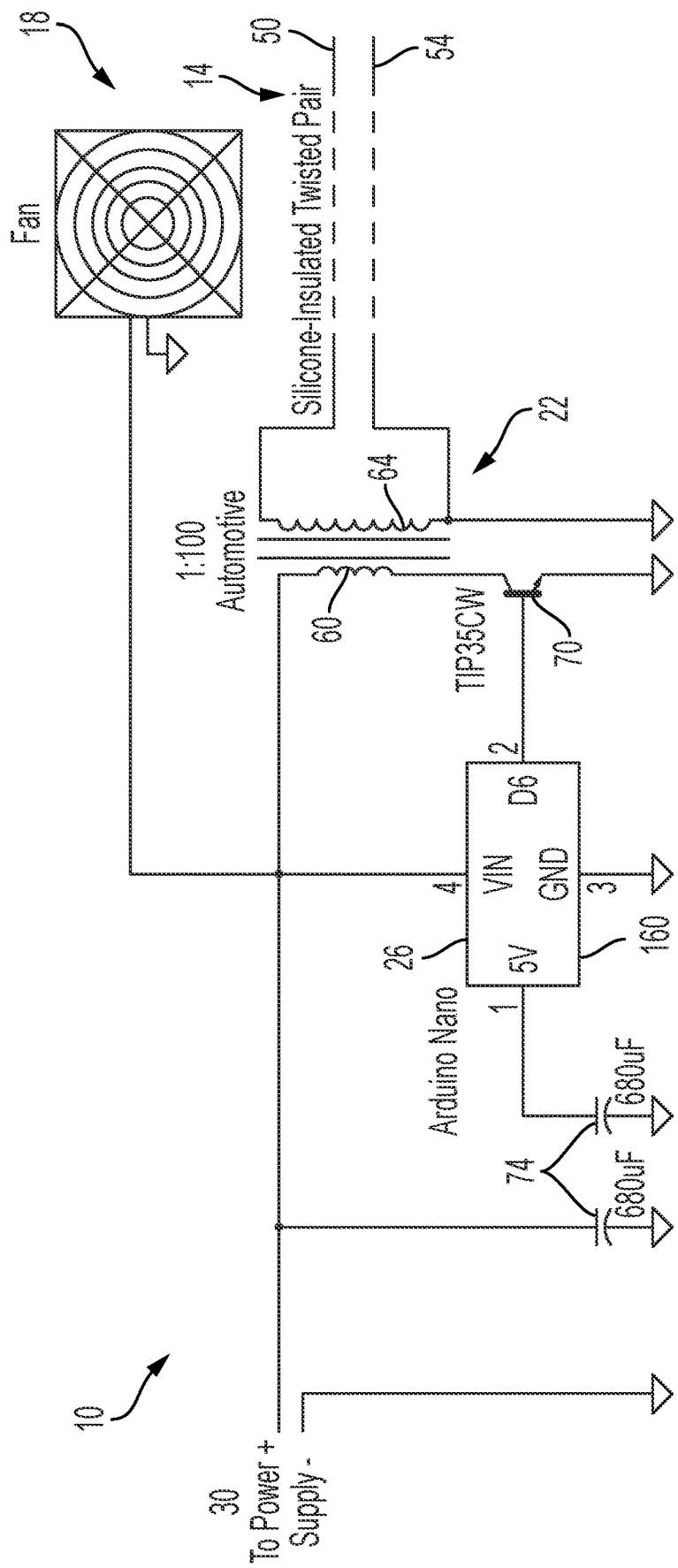
FIG. 1 is a schematic of an ozone generation system according to one construction.

Before any constructions of the invention are explained in detail, it is to be understood that the invention is not limited in its application to the details of construction and the arrangement of components set forth in the following description or illustrated in the following drawings. The invention is capable of other constructions and of being practiced or of being carried out in various ways.

The COVID-19 epidemic has accumulated well over 4 million cases worldwide to date, and is continuing to grow. Severe acute respiratory syndrome coronavirus 2 (SARS-COV-2), the pathogen responsible for the COVID-19 epidemic, has been classified as highly contagious through analysis of outbreak dynamics worldwide. Further studies have shown that SARS-COV-2 has the ability to remain stable on a variety of surfaces, resulting in its ability to spread rapidly. Interestingly, recent work has highlighted its ability to remain stable on items such as the shoes of medical care workers, allowing shoes to act as a vector for viral transmission. Given the rapid spread of SARS-COV-2 and its high stability, there is an increasing need for effective sterilization techniques that can sterilize a myriad of items which may carry SARS-COV-2.

The global scientific community has performed extensive work to characterize novel sterilization systems for decontamination of potentially-contaminated items, from disposable N95 respirators to hospital gowns and even cell phones. However, a majority of these techniques are designed and built for high-throughput sterilization in hospital and clinical settings. These systems are often expensive and environmentally unsustainable. To this end, the present application discloses sterilization systems 10 that include environmentally sustainable ozone generators, which can be easily built and scaled to a variety of sterilization uses.

FIGS. 1-4 illustrate a sterilization system 10 according to one construction. Hereinafter the sterilization system 10 may be referred to as an ozone generation system, ozone system, or a system. The system 10 includes an ozone generator 14, a fan 18, a transformer 22, a controller 26, and a power source 30.

In the illustrated construction, the ozone generator 14 includes a first electrode or conductor 50 and a second electrode or conductor 54 that are twisted (e.g., interleaved, intertwined) with one another. More specifically, each of the first and second electrodes 50, 54 are formed from wire that is insulated with an ozone-resistant, high-dielectric strength material. In the illustrated construction, the wire is insulated with silicone rubber, but other suitable materials may be used. Moreover, the first and second electrodes 50, 54 may be configured in a helical twisted pair with the density of twisting such that an airspace present therebetween is sufficient and appropriate to promote the generation of a corona discharge.

In one construction, for example, the first and second electrodes 50, 54 may be configured in a helical twisted pair with the density of twisting such that 0.1 mm to 10 mm of airspace is present therebetween at the widest separation points. In other constructions, for example, the first and second electrodes 50, 54 may be configured in a helical twisted pair with the density of twisting such that 0.5 mm to 2 mm of airspace is present therebetween at the widest separation points. In other constructions, for example, the first and second electrodes 50, 54 may be configured in a helical twisted pair with the density of twisting such that 0.5 mm to 1 mm of airspace is present therebetween at the widest separation points. The length of the first and second electrodes 50, 54, when twisted, may be 1.5 meters, although the length may be any suitable length. Accordingly, the length of the first and second electrodes 50, 54, when twisted, may be longer or shorter than 1.5 meters. In some constructions, for example, the length of the first and second electrodes 50, 54, when twisted, may range from 0.5 meters to 3 meters. The twist density and length, which may vary as appropriate, is configured to provide an adequate volume of a high-electric field region between the first and second electrodes 50, 54. Moreover, these constraints may vary also depending on the specific electronics selected for the power source 30 and the particular use (e.g., items to be treated). Additionally, the first and second electrodes 50, 54 may be coiled or wrapped in an arrangement (FIGS. 2, 3) that maximizes the exposed high-electric field region to the flow of air therethrough.

In the constructions illustrated herein, the controller 26 (e.g., microcontroller) is coupled to a printed circuit board 28 (e.g., a nano printed circuit board provided by Arduino), although other controllers or application-specific integrated circuits or similar control devices may be implemented. In other constructions (such as that shown in FIGS. 12-14), the transformer 22 may be a high-voltage flyback transformer (e.g., a line output transformer). In the illustrated construction, the transformer 22 is an induction coil, such as, for example, an ignition coil (e.g., spark ignition coil) typically used in automotive applications. In the illustrated construction, the transformer 22 includes a primary side 60 that is coupled to the controller 26 and a secondary side 64 that is coupled to the ozone generator 14 (e.g., either or both of the first or second electrodes 50, 54). A power transistor 70 is positioned between and coupled to the controller 26 and the primary side 60 of the transformer 22. The power source 30 is a high-voltage power source and may be an AC or DC power source. In the illustrated construction, the power source 30 is a DC power source and has a power rating of 12V and 2 A, although other suitable power ratings are possible.

Figure 2:
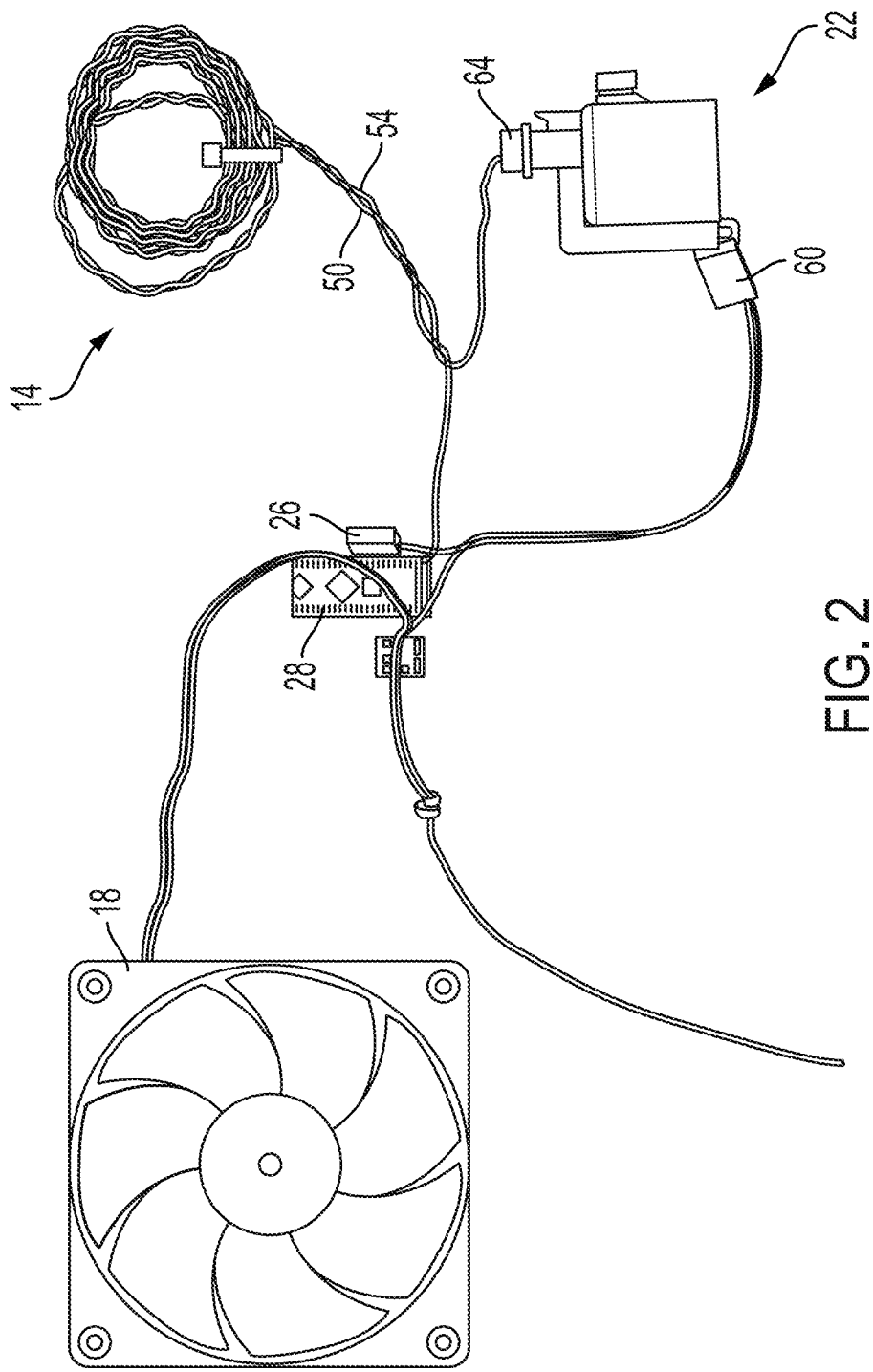
FIG. 2 is a partially exploded view of the ozone generation system of FIG. 1.

As shown in FIGS. 1-2, the ozone generator 14 is in electrical communication with the secondary side 64 of the transformer 22 and the controller 26. In particular, the first and second electrodes 50, 54 are in electrical communication with the secondary side 64 of the transformer 22. In the illustrated constructions, one of the first or second electrodes 50, 54 is coupled to the secondary side 64 of the transformer 22, and the other of the first or second electrodes 50, 54 is coupled to the controller 26. The primary side 60 of the transformer 22, the fan 18, and the power source 30 are in electrical communication with the controller 26. The controller 26 provides a pulse-width modulated control signal that is applied to a power transistor 70, which drives the primary side 60 of the transformer 22, discussed in greater detail below. The controller 26 may also include one or more capacitors 74, which ensure the voltage supply to the power transistor 70 and controller 26 remains stable during the operation of the system 10. This is because the capacitors 74 decouple the power source from the controller 26. The capacitors 74 may have any suitable capacitance. In some constructions, the capacitors 74 may have a capacitance ranging from 1 µF to 2200 µF. In the constructions shown in FIGS. 1-9, there are two capacitors each having a capacitance of 680 µF. In other constructions, the capacitors 74 may have any suitable capacitance including, but not limited to and provided only by way of example, 1 µF, 700 µF, or 1100 µF, etc. In the illustrated construction, the capacitors 74 are electrolytic capacitors.

Figure 10:
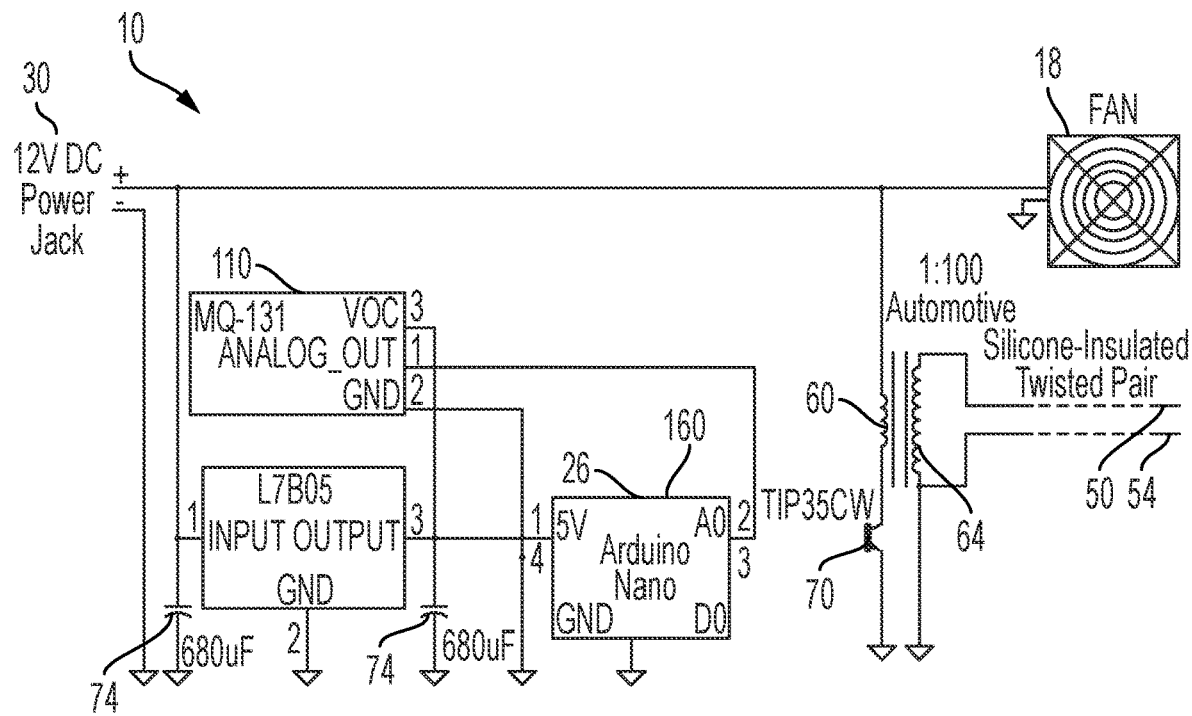
FIG. 10 is a schematic of an ozone generation system according to another construction.
Figure 11:
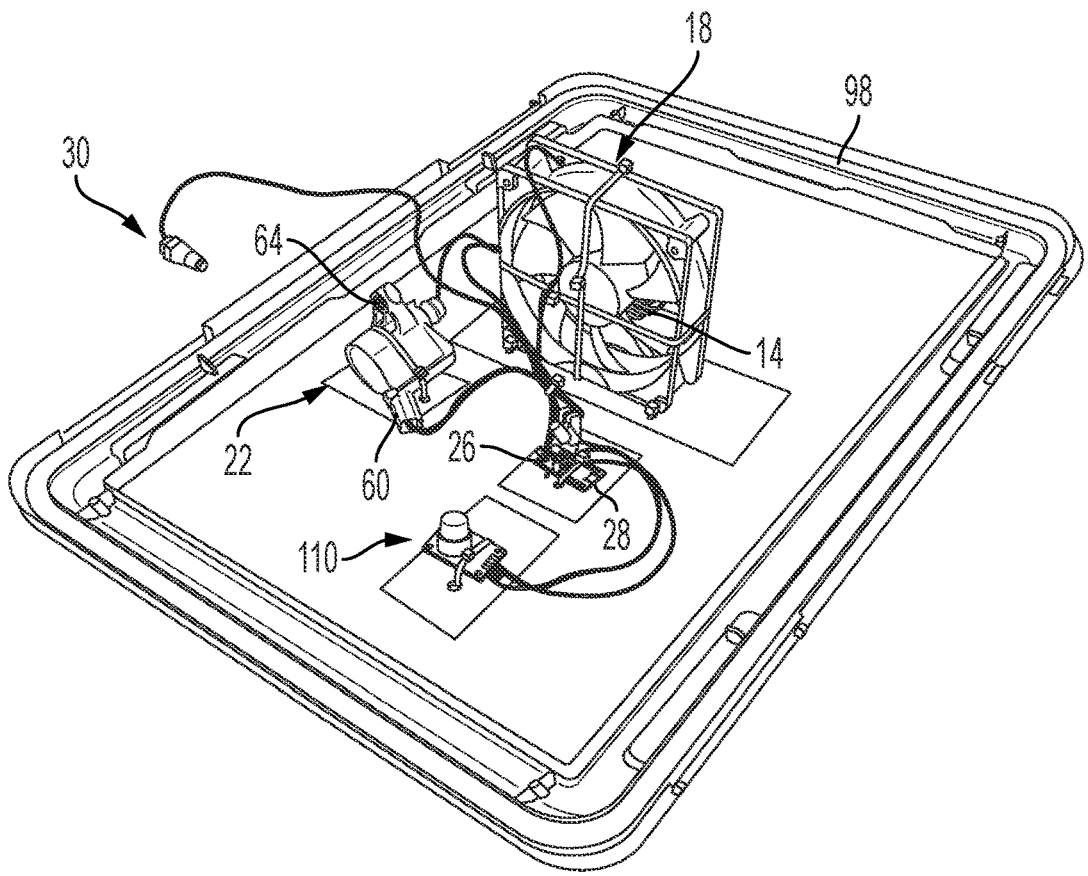
FIG. 11 is a bottom perspective view of the lid of FIG. 5 supporting the ozone generation system of FIG. 10.

FIGS. 10-11 illustrate an ozone generation system 10 according to another construction. The ozone generation system 10 of FIGS. 10-11 is similar to the ozone generation system of FIGS. 1-4, so like reference numerals will be used for like structure and only the differences discussed herein. As shown in FIGS. 10-11, the ozone generation system 10 includes one or more ozone level sensors 110 for measuring the level of ozone. The one or more ozone level sensors are in communication with and provide feedback to the controller 26. In some constructions the ozone sensor may be a MQ-131 ozone sensor. The ozone level sensor 110 is preferably positioned adjacent to the ozone generator 14 or generally in the vicinity of the ozone generator 14. In the illustrated construction, the sensor 110 is spaced apart from and electrically coupled to the circuit board 28 (FIGS. 10-11).

Further with respect to FIGS. 10-11, the ozone generation system 10 may further include a linear regulator 120 for maintaining a constant voltage output to the controller 26. The linear regulator 120 is in electrical communication with the power source 30 and the controller 26. The controller 26 is powered from the output voltage of the linear regulator 120. The one or more capacitors 74 are in electrical communication with the linear regulator 120 to decouple the power source from the controller 26. That is, the voltage from the power source 30 is buffered by one or more capacitors 74 and the output voltage of the linear regulator 120 is buffered by one or more capacitors 74. Here, at least one of the capacitors 74 is in electrical communication with the power source 30 and an input of the linear regulator 120, and at least one of the capacitors 74 is in electrical communication with an output of the linear regulator 120 and the controller 26. In other constructions, both capacitors 74 or other capacitors may be in electrical communication with the input of the linear regulator 120. The output voltage of the linear regulator 120 is configured to match the voltage rating of the controller 26, which in this case is 5V. Therefore, in the illustrated construction, the output voltage of the linear regulator 120 is preferably 5 V. In other embodiments, rating of the controller 26 and the corresponding output voltage of the linear regulator 120 may have other suitable values, such as, but not limited to, 3.3V.

Figure 12:
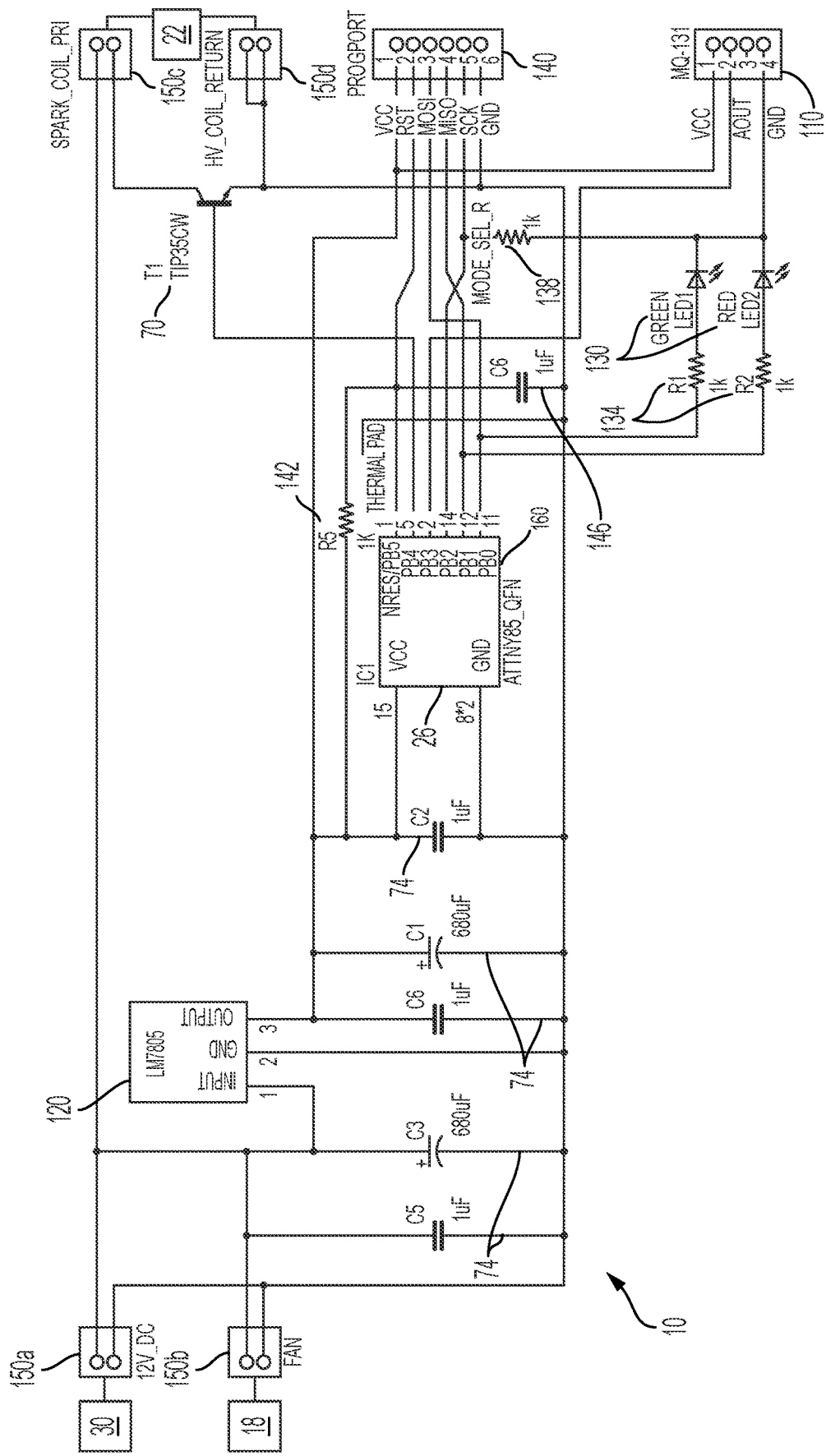
FIG. 12 is a schematic of an ozone generation system according to another construction.
Figure 13:
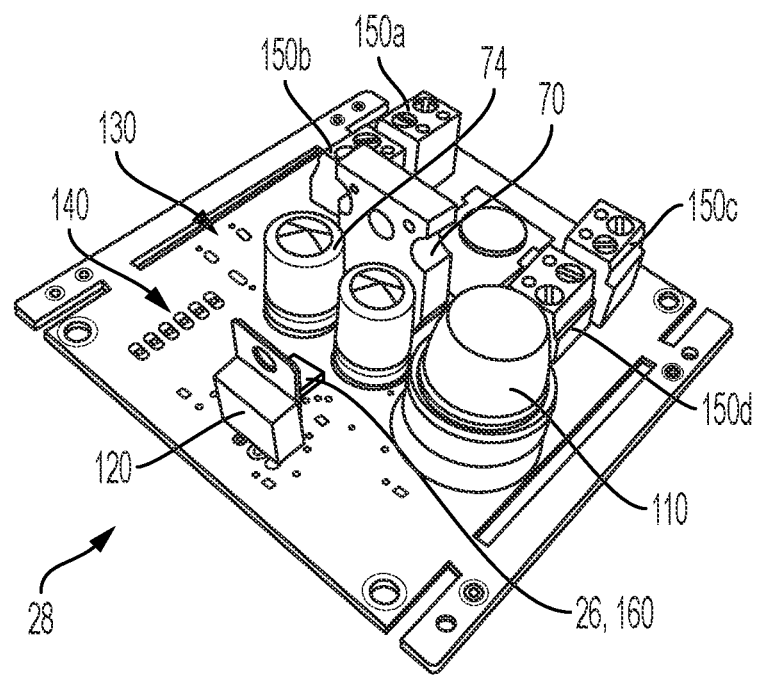
FIG. 13 is a printed circuit board of the ozone generation system of FIG. 12.
Figure 14:
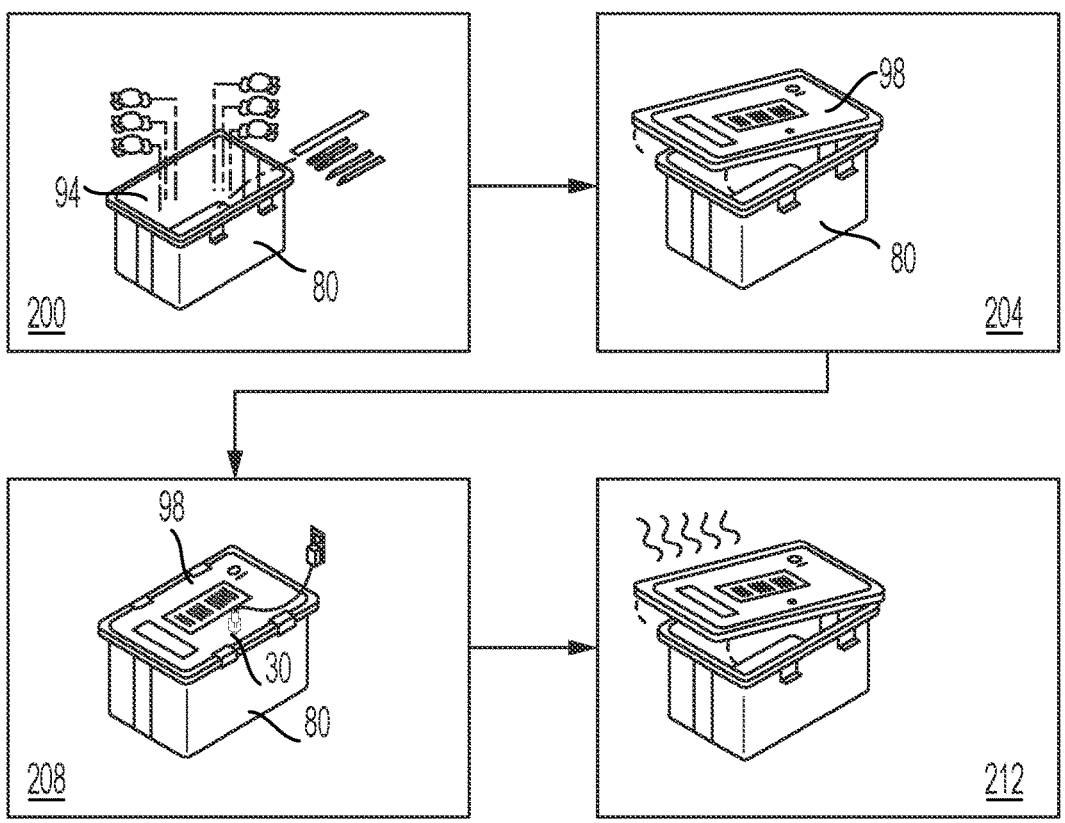
FIG. 14 illustrates a method of use of the ozone generation systems of FIGS. 1-13.

FIGS. 12-13 illustrate an ozone generation system 10 according to another construction. The ozone generation system 10 of FIGS. 12-13 is similar to the ozone generation system of FIGS. 1-3 and FIGS. 10-11, so like reference numerals will be used for like structure and only the differences discussed herein. Like the construction of FIGS. 10-11, in the construction of FIGS. 12-13, the voltage from the power source 30 is buffered by one or more capacitors 74 and the output voltage of the linear regulator 120 is buffered by one or more capacitors 74. Here, at least two of the capacitors 74 are in electrical communication with the power source 30 and the input of the linear regulator 120, and at least two of the capacitors 74 are in electrical communication with the output of the linear regulator 120 and the controller 26. In other constructions more or fewer of the capacitors 74 or other capacitors may be in electrical communication with the input and the output of the linear regulator 120. In this construction, one or more of the capacitors is an electrolytic capacitor. The capacitors may have any suitable capacitance. In some constructions, the capacitors 74 may have a capacitance ranging from 1 µF to 2200 µF. In the construction of FIGS. 13-14, one of the capacitors in communication with the input of the linear regulator has a capacitance of 680 µF and the other of the capacitors in communication with the input of the linear regulator 120 has a capacitance of 1 µF. In other constructions, the capacitors 74 may have any suitable capacitance including, but not limited to and provided only by way of example, 1 µF, 700 µF, or 1100 µF, etc. Similarly, one of the capacitors in communication with the output of the linear regulator has a capacitance of 680 µF and one or more of the other capacitors 74 in communication with the output of the linear regulator 120 has a capacitance of 1 µF. Here, again, the output voltage of the linear regulator 120 can be 5 volts.

In the construction of FIGS. 12-13, the controller 26 provides indication of the power status of the system 10 and the ozone-generation status of the system 10 by the use of light-emitting diodes (LEDs) 130. In the illustrated construction, one of the LEDs emits a first color (e.g., green) when the power status is "ON" and another of the LEDs emits a second color (e.g., red) when the power status is "OFF." In other constructions, the LEDs may have other suitable colors. In still other constructions, the LEDs may use any suitable means of notifying the user of the status of the system, including different light emitting patterns (e.g., LEDs that blink in different light patterns). In still other constructions, there may be more or fewer LEDs. Current-limiting resistors 134 are connected in series with LEDs 130 in order to limit the maximum current that flows through them. By way of example, typical indicator LED drive current should not exceed 20 mA, so for a 5V supply and a 3V forward-drop LED, resistors should be no lower than 10062. For visibility, typical drive current should be no less than 1 mA, so resistor values should be no greater than 2 kΩ. Therefore, the resistors 134 may have any suitable resistance ranging from 100Ω to 2 kΩ, but in the illustrated construction the resistors are 1 kΩ resistors.

Further with respect to FIGS. 12-13, the ozone generation system 10 further includes a controller programing port 140 that has an external programmer pin that allows the controller 26 to be programmed with firmware when the ozone generation system 10 is initially constructed. A resistor 142 (e.g., a pullup resistor) and capacitor 146 (e.g., a filter capacitor) are provided on the reset-controlling pin of the controller 26 to assert its reset-state as FALSE except during programming. The resistors 142 may have any suitable resistance, but in the illustrated construction the resistors are 1 kΩ resistors. Generally, external programmer pins typically will not source more than 40 mA, so the resistor 142 should be no less than 125Ω and no greater than 60 kΩ for stability. The capacitor 146 may have any suitable capacitance, but in the illustrated construction the capacitor 146 is a 1 uF capacitor.

The ozone sensor 110 in any of these constructions is optional. In the illustrated construction of FIGS. 12-13, the external programming pin is also a mode selection pin. Moreover, a resistor 138 in communication with the mode selection pin may be provided to indicate to the controller 26 whether or not the ozone sensor 110 is connected to thereto. The resistor 138 may have any suitable resistance, but in the illustrated construction the resistors are 1 kΩ resistors. As noted above, external programming pins typically do not source more than 40 mA, so the resistor 138 should be no less than 125Ω. Moreover, the input pullup resistance in the illustrated constructed is >20 k Ω, so to ensure a decisive digital "1", the mode selection resistance of the resistor 138 should be no greater than half this value (10 kΩ).

In the construction of FIGS. 12-13, the printed circuit board is used to consolidate the electrical connections of the ozone generation system 10. Moreover, for ease of manufacturability, terminal blocks 150a-150d are used to couple the power source 30, the fan 18, the electrodes 50, 54 (not shown in FIGS. 12 and 13) of the ozone generator 14, and the transformer 22 to the printed circuit board 28.

In any of the constructions, the ozone generation system 10 may further include a timer 160 (e.g., a software timer or duty cycle timer). In the illustrated construction, the timer 160 is implemented in the software onboard the control 26.

Figure 3:
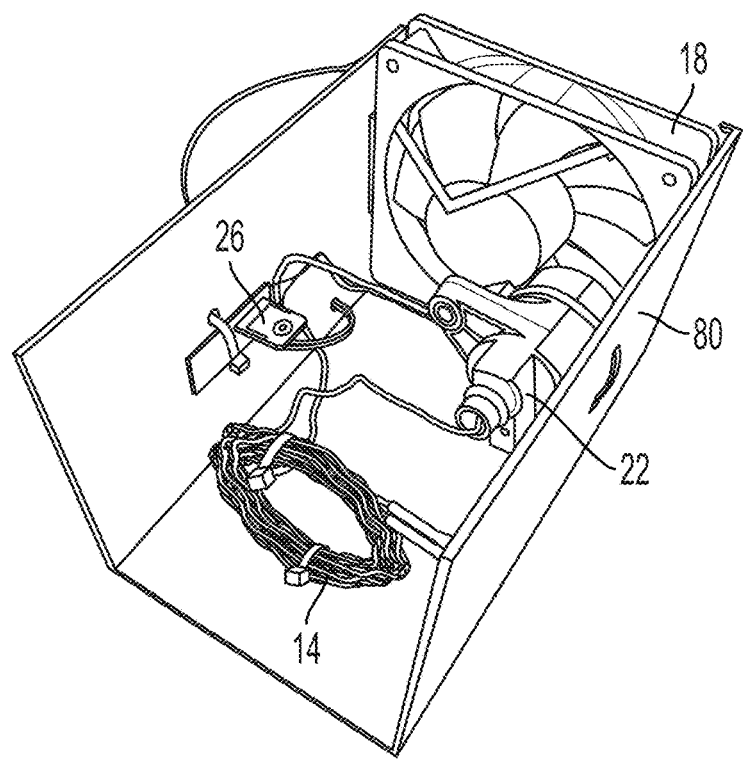
FIG. 3 is a perspective view of a housing supporting the ozone generation system of FIG. 1.
Figure 4:
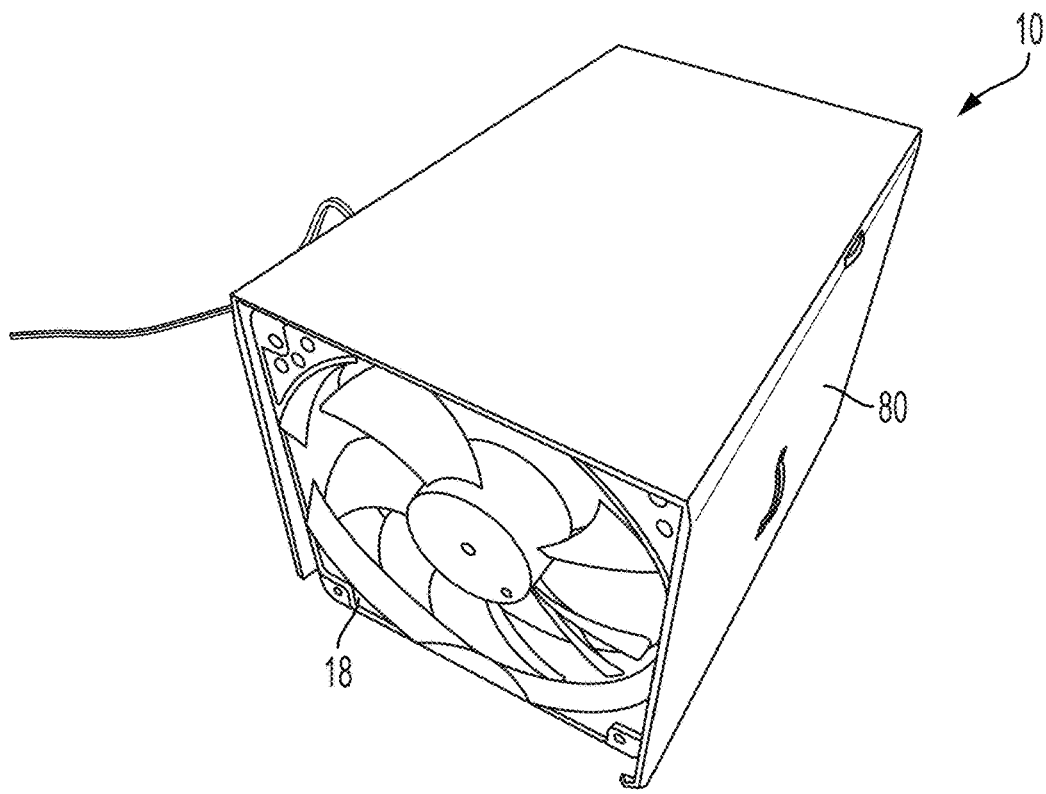
FIG. 4 is a perspective view of the ozone generation system enclosed in the housing of FIG. 3.
Figure 5:
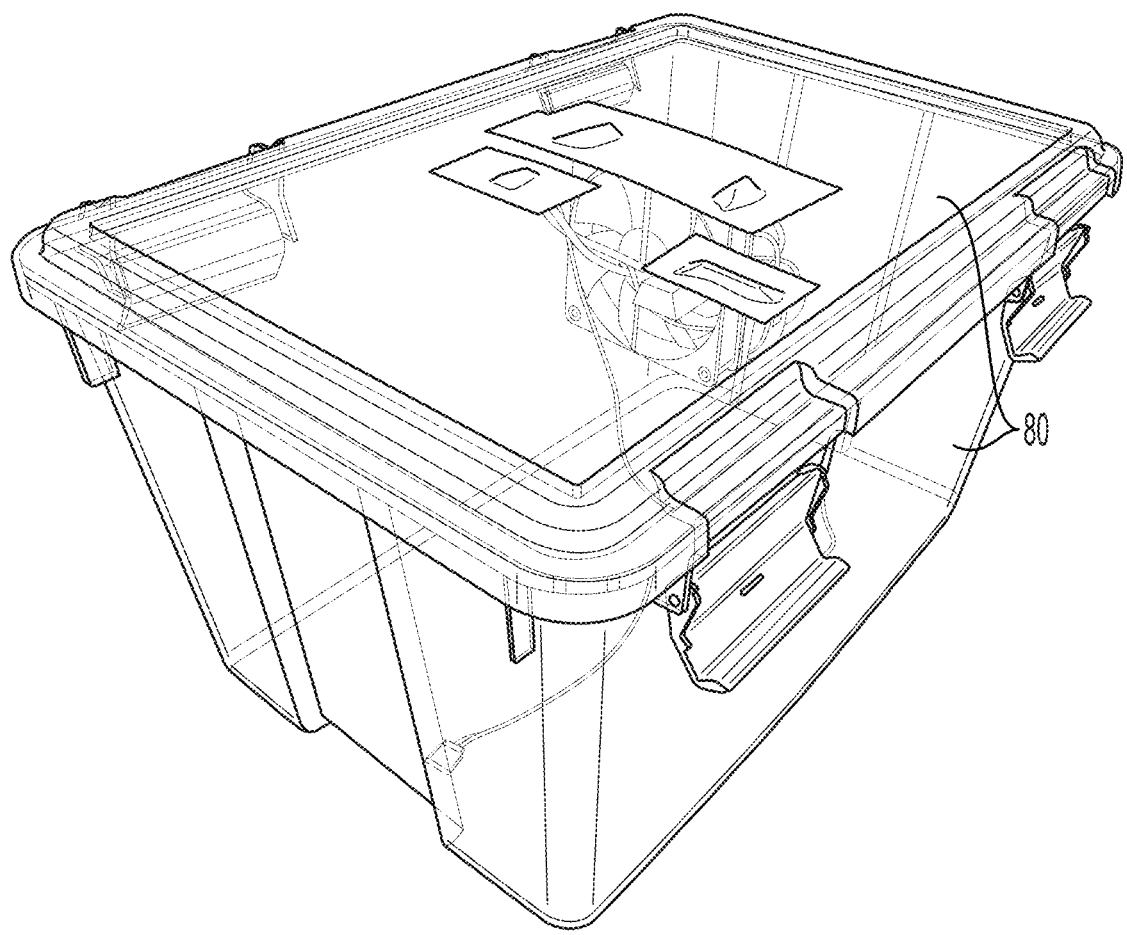
FIG. 5 is a perspective view of another housing supporting the ozone generation system of FIG. 1, the housing including a body and a lid.
Figure 6:
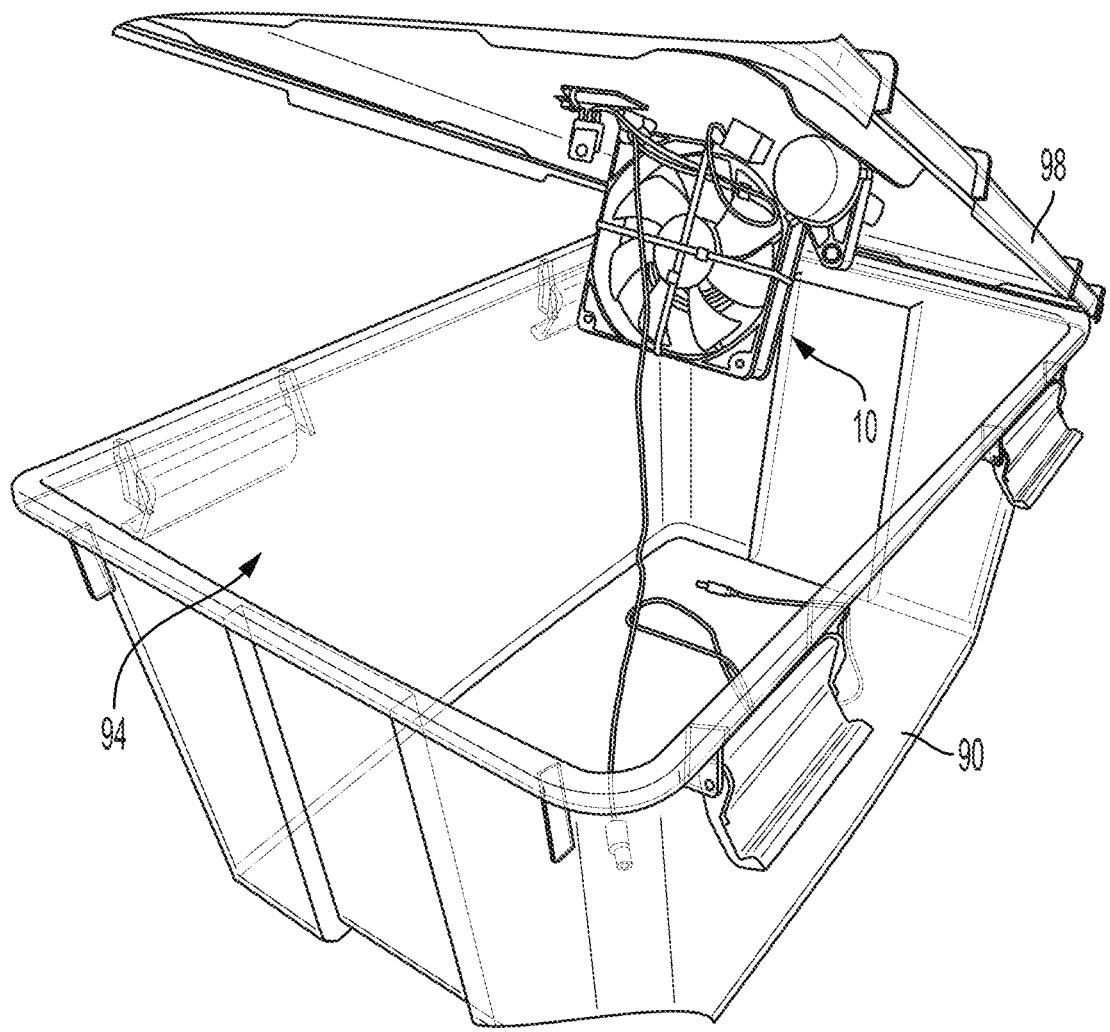
FIG. 6 is another perspective view of the housing of FIG. 5.
Figure 7:
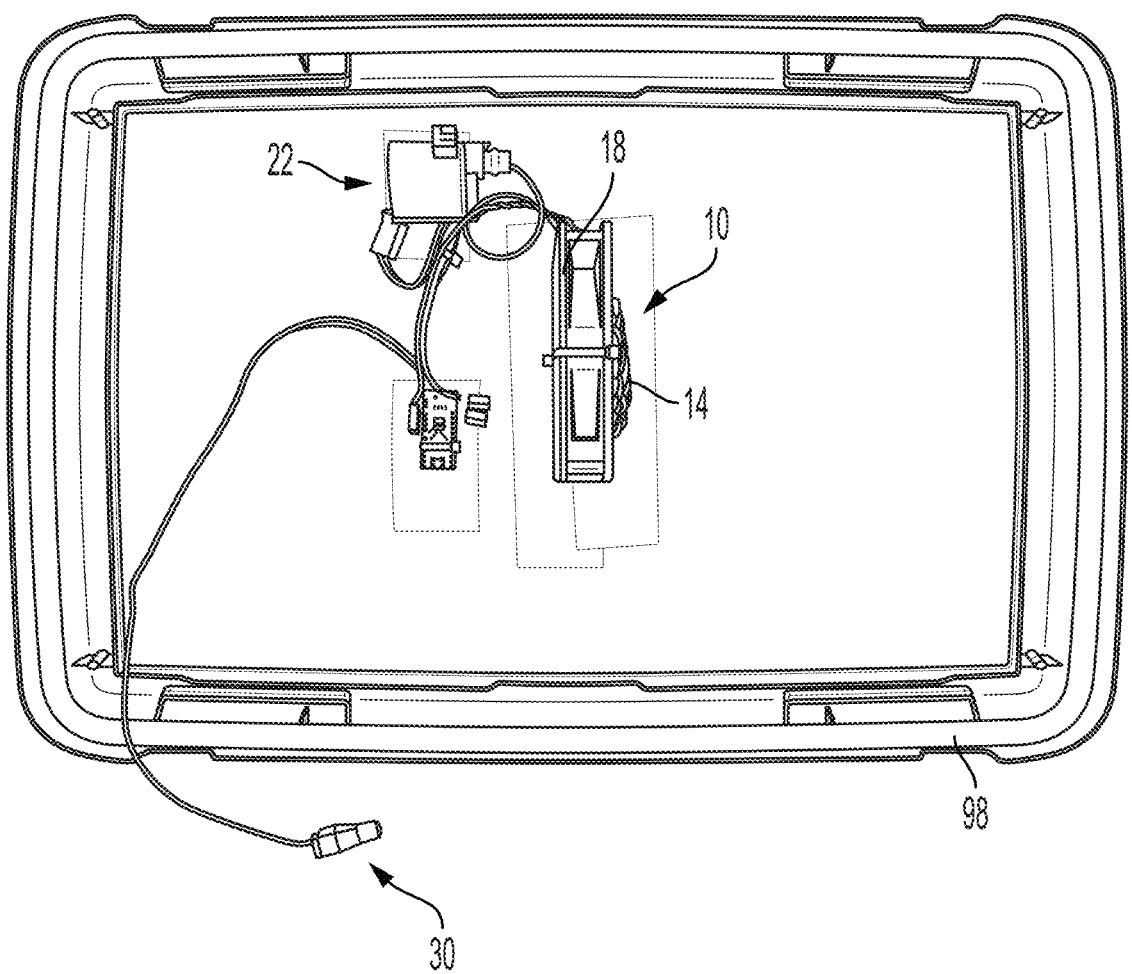
FIG. 7 is a bottom view of the lid of FIG. 5.
Figure 8:
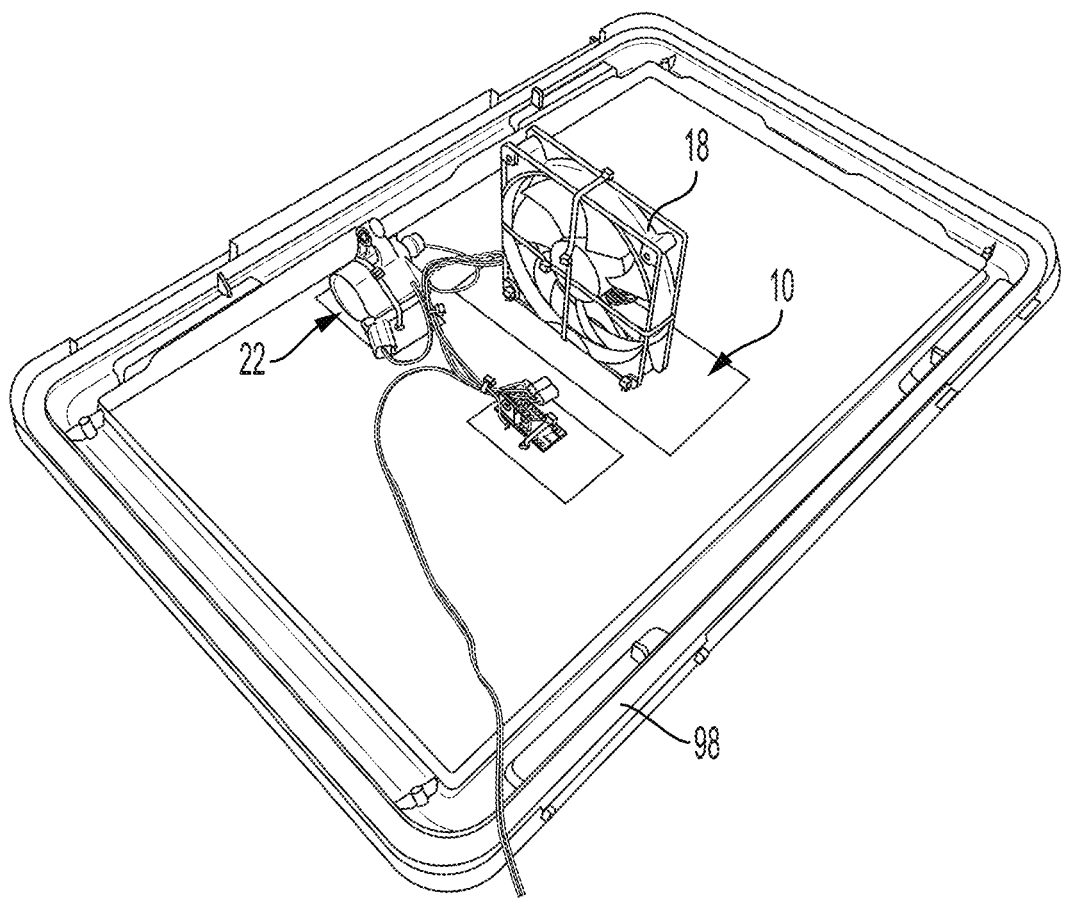
FIG. 8 is a bottom perspective view of the lid of FIG. 5.
Figure 9:
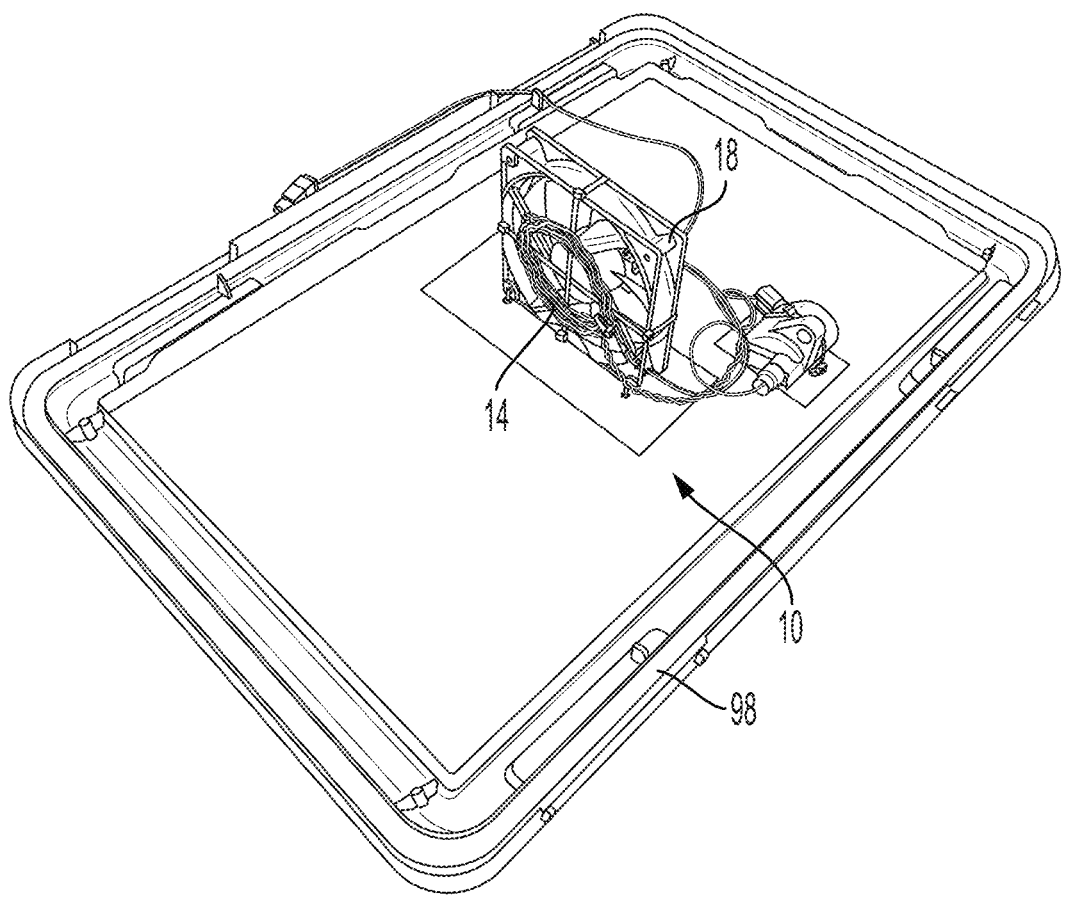
FIG. 9 is another bottom perspective view of the lid of FIG. 5.

As shown in FIGS. 3-9, the ozone generation system 10 can be at least partially enclosed within and supported by a housing or chassis 80. In the construction of FIGS. 3 and 4, the fan 18 is positioned at an opening of the housing 80 and the ozone generator 14 is spaced apart from the fan 18 and adjacent another opening of the housing 80. In other embodiments, the fan 18 may be positioned adjacent to or directly coupled with the ozone generator 14 (FIGS. 5-9). The transformer 22 and the controller 26 are positioned on and coupled to other surfaces of the housing 80. The fan 18 circulates air across the ozone generator 14 (e.g., the coiled first and second electrodes 50, 54). In the construction of FIGS. 5-9, the housing 80 includes a body portion 90 that has a sterilization chamber 94 and a lid 98 (e.g., closure element). The chamber 94 of the body 90 may receive materials to be sterilized and disinfected, and the lid 98 may be removably secured to the body 90 to close the chamber 94 and to ensure an airtight seal. As shown, the ozone generation system 10 is enclosed within the chamber 94. Specifically, the ozone generation system 10 is coupled to lid 98, and any attachment points are sealed in place by an adhesive sealing material (e.g., adhesive-backed aluminum tape, fasteners, etc.). The ozone generation system 10 or various features thereof may be coupled to other surfaces of the housing 80 in other constructions. Moreover, the ozone generation system 10 may be positioned in an auxiliary container (not shown) that is fluid communication with the housing 80 such that ozone generated within the auxiliary container can flow to the storage chamber of the housing 80. The housing 80 may be formed from any suitable material (e.g., cardboard, plastic, metal, etc.).

In use, the ozone generation system 10 ionizes atmospheric oxygen through the application of corona discharge. More specifically, the ozone generation system 10 develops a high potential electric field to generate ozone via corona discharge. Corona discharge occurs when a region of high electric field strength causes ionization of air or other gases without the incidence of dielectric breakdown. The ionization of these gases results in recombination of a percentage of oxygen radicals into triatomic oxygen (i.e., ozone). Ozone is a well-characterized biocidal agent, even in relatively low concentrations. This process allows ozone to be produced without any chemical feedstock, making it a highly sustainable and scalable disinfectant source. Accordingly, the high electric field is generated in the airspace located between the first and second electrodes 50, 54. Materials such as, for example, consumer supplies (e.g., goods and clothing) or medical supplies or personal protective equipment (e.g., masks, re-usable medical equipment, and clothing) placed adjacent to or near the electrodes 50, 54 or within the housing 80 may be sterilized or disinfected by the ozone created by the system 10. In the construction of FIGS. 3-4, the materials may be positioned adjacent the ozone generator 14. In the construction of FIGS. 5-9, the materials may be positioned within the chamber 94. Also, the system 10 may be placed in a room or space and used to disinfect or sterilize the same. Further, the system 10 may be used in industrial ozone production and to produce a process gas.

Figure 20:
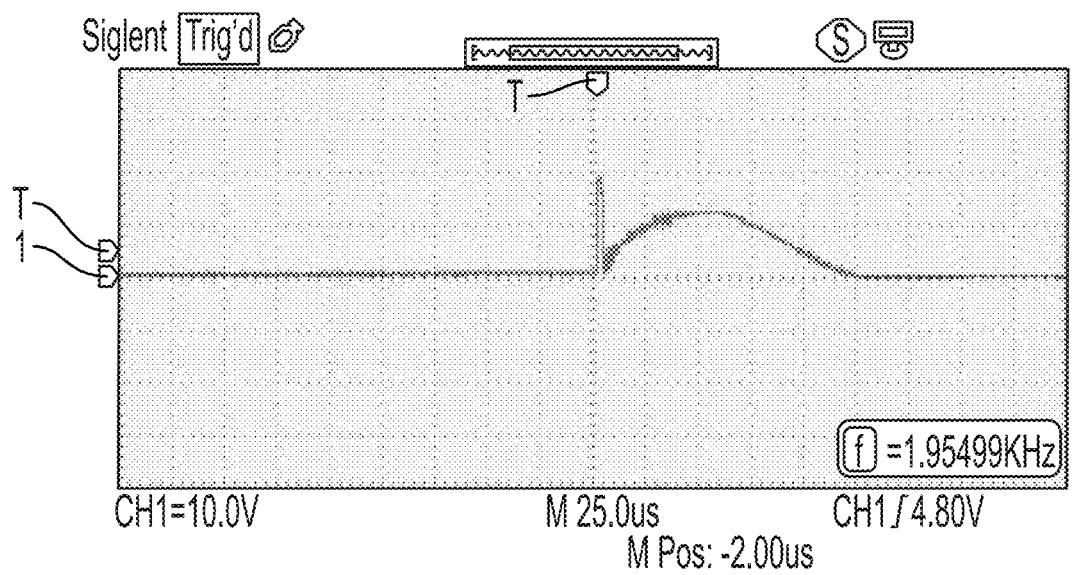
FIG. 20 illustrates an oscilloscope plot showing the voltage between the collector and emitter of an element of the systems of FIG. 1-13 during one duty cycle of operation.

The electronic circuits of the system 10 described herein are designed to provide pulsed high voltage to the ozone generator 14 using the transformer 22 and transistor 70. The transistor 70 is turned on and off by the controller 26 (e.g., typically at 980 Hz) using a pulse-width modulation (PWM) signal. When the transistor 70 is turned on, electric current starts flowing in the primary winding 60 of the transformer 22. The inductance of the transformer 22 is high because it has an air gap, so the current through the generator 14 rises gradually when voltage is applied to it by the transistor 70 turning on. When the transistor 70 turns off, the current through the transformer 22 persists, resulting in a high voltage (190 V initially and 130V for a sustained period for the transistor 70) being generated across the primary winding 60 of the transformer 22. An exemplary oscilloscope plot of the voltage across the transistor 70 during one cycle of operation is depicted in FIG. 20. Vertical divisions in FIG. 20 are 100 V/div and horizontal divisions are 25 us/div. Voltage is measured through a 10× attenuation probe, so voltage values are 10× the values shown here. The transistor 70 briefly operates in dielectric breakdown, which limits the peak voltage across the primary winding 60 of the transformer 22. The limitation of voltage prevents damage to the generator 14, and also allows the flow of current to persist for longer, leading to a more sustained corona discharge at the ozone generator 14. This voltage is magnified by approximately 100× at the secondary winding 64 of the transformer, which allows approximately 15 kV to be developed in the ozone generator 14. Corona discharge occurs and ozone is formed by the ionization and recombination of atmospheric oxygen.

Either or both of the ozone sensor 110 or the timer 160 may help to determine or adjust the amount of ozone levels within the chamber 94. That is, the materials within the sterilization chamber 94 or space surrounding the system 10 (e.g., ozone generator 14) may be exposed to a pre-determined level of ozone, which may be determined independently or in conjunction with feedback from the ozone sensor 110, the timer 160, or both the sensor 110 and the timer 160. When the sensor 110 is used, the system 10 may operate in an automatic mode (e.g., variable ozone mode). When part of the system 10, the one or more ozone level sensors 110 may be in communication with and provide feedback to the controller 26 such that the controller 26 may adjust ozone production output to maintain a pre-determined level of ozone within the sterilization chamber 94 or space surrounding the system 10 (e.g., ozone generator 14). When the sensor 110 is not used the system may operate in a constant ozone mode. When the one or more ozone level sensors 110 are not in use, the controller 26 may determine ozone production using the timer and the number of PWM signals sent to the transformer. The duty cycle of the PWM signal may be 50% duty cycles in some constructions, although the duty cycles may have other suitable values. For example, the pre-determined level of ozone may be determined by a pre-determined amount of time that the materials are exposed to constant ozone. The pre-determined amount of time may be determined by the amount of time required for the controller 26 to send a pre-determined amount of PWM signals (and therefore undergo a predetermined number of duty cycles). The systems may thus operate one of multiple modes depending on whether the ozone sensor 110, the timer 160, or both are used.

An exemplary method of assembling the sterilization system 10 includes forming the ozone generator 14. The ozone generator 14 is formed by twisting a first electrode 50 with a second electrode 54. The method may further include enabling the controller 26 to communicate with the ozone generator 14 and the power source 30. The ozone generator 14 may be in communication with the controller 26 by coupling the ozone generator 14 to the transformer 22. More specifically, the method may include coupling the controller 26 to the primary side 60 of the transformer 22 and coupling the ozone generator 14 to the secondary side 64 of the transformer 22. The method further includes positioning the fan 18 relative to the ozone generator 14 such that airflow may flow from the fan 18 to the ozone generator 14. The method further includes positioning the ozone generator 14 and power source 30 into the housing 80. The method further includes positioning the ozone generator 14, the power source 30, the controller, 26, the transformer 22, and the fan 18 into the housing 80.

Once assembled, FIG. 14 shows an exemplary method of use of a sterilization system 10 to treat materials contained within the housing 80. At step 200, the method includes placing materials to be sanitized into the housing 80. At step 204, the method includes securing the housing 80 with the lid 98 to seal the chamber 94. At step 208, the method includes powering the system 10 with the power source 30 to generate ozone by guiding air over an ozone generator 14, and treating the material positioned with the chamber 94 during a treatment cycle. In some cases, the treatment cycle may run (e.g., ozone may be generated and maintained) for a first time period (e.g., 53 minutes) to sanitize (e.g., 99.9% viral inactivation) the materials. In some cases, the treatment cycle may run (e.g., ozone may be generated and maintained) for a second time period (e.g., 150 minutes) to sterilize (e.g., 99.999% viral inactivation) the materials. At step 212, the method further includes removing power from the system after the treatment cycle is finished and removing the lid (in a well-ventilated space). After a waiting period (e.g., 10 minutes to 15 minutes) during which the ozone dissipates from the chamber, the materials may be removed for reuse.

Figure 15:
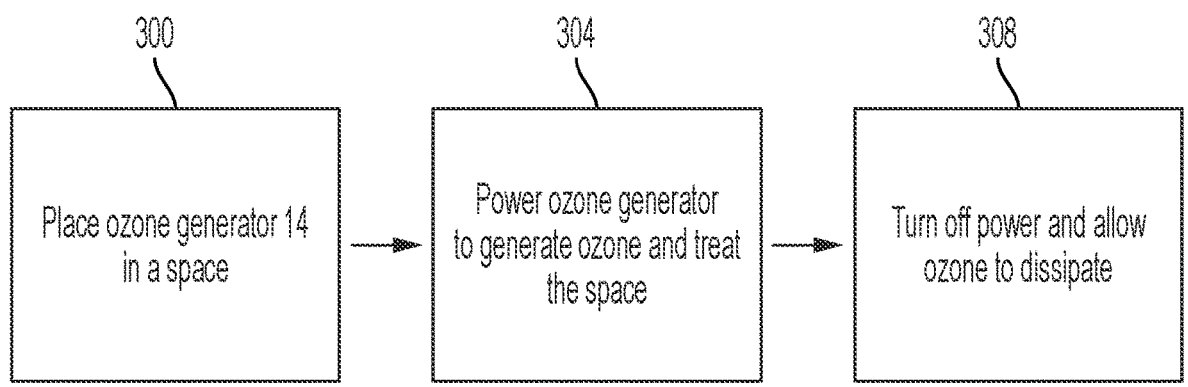
FIG. 15 illustrates a method of use of the ozone generation systems of FIGS. 1-13.

FIG. 15 shows an exemplary method of use of a sterilization system 10 to treat a space (e.g., room or area surrounding the system 10). At step 300, the method includes placing the system 10 in the space. At step 304, the method includes powering the system 10 with the power source 30 to generate ozone by guiding air over an ozone generator 14, and treating the space during a treatment cycle. The treatment cycle may be determined by the size of the space being treated. At step 308, the method further includes removing power from the system after the treatment cycle is finished and allowing the ozone to dissipate over the waiting period.

Table 1 below outlines exemplary recommended dosages to achieve certain log reductions in viral contaminants, based on Inactivation of Influenza Virus by Ozone Gas, as most other viruses, including bacteriophages, are more sensitive to ozone than influenza. Results during validation virucidal activity using P22 bacteriophages as a proxy for SARS-COV-2 achieved a 6-log reduction and supported these recommended dosages.

TABLE 1

Dosage chart displaying recommended treatment times at 20 ppm of ozone gas to achieve specific reductions in viral load.

| Level of Inactivation of Viral Load Achieved | Treatment Length (min) @ 20 ppm of Ozone Gas | Dosage Achieved (ppm min) |
| --- | --- | --- |
| 90% | 17.5 | 350 |
| 99% | 35 | 700 |
| 99.9% | 52.5 | 1,050 |
| 99.99% | 90 | 1,800 |
| 99.999% | 135 | 2,700 |
| >99.999% | 150 | 3,000 |

At 99.9% inactivation, also known as a 4-$\log_{10}$ reduction, achieves sanitization of the viral load. At 99.999% inactivation, or a 6-$\log_{10}$ reduction, achieves sterilization of the viral load, which would be the required level of disinfection for an N95 or equivalent respirator, especially in a healthcare setting.

The sterilization systems 10 described herein are constructed from a sealed ambient-pressure chamber and a low-cost ozone generator, which when combined, allow a prescribed ozone concentration to be achieved within the chamber or space for a sustained period of time. The sealed ambient-pressure chamber may be constructed from one of a number of commonly-available plastic tubs or bins. The low-cost ozone generator is constructed from widely-available automotive and consumer electronics, allowing adequate ozone to be generated without specialty components. The ozone treatment system does not require high power input, and may be powered from any 12V DC supply capable of providing at least 2 amps, including automotive power sources or batteries in the case where an AC grid supply is not available. In order to ensure a narrow range of ozone levels in the treatment chamber, the ozone concentration sensor may be coupled with the circuitry, but in certain contexts where ozone concentration does not need to be closely controlled, a timer may be used to control the ozone accumulation within the chamber instead.

In addition to low material cost, the parts used for the sterilization systems 10 described herein are available outside of medical supply chains. This allows for the system to be scaled to the needs of businesses, educational institutions, and small healthcare providers even during present shortages.

Validation Processes

The following methods were used to quantitatively demonstrate the efficacy of the sterilization systems 10 for sterilization. Surgical N95 respirators were selected for this study due to their well-defined standards for minimum performance. Additionally, the sterilization of other items (e.g., shoes, etc.) using the sterilization systems 10 were also studied through a qualitative evaluation of degradation under typical treatment conditions.

Validating a system for sterilization of N95 respirators involves not only biological validation but also consideration of the effects of sterilization on NIOSH-dictated standards such as fit, inhalation resistance, and most importantly a N95's required filtration efficiency of 95% or higher for non-oily solid and liquid aerosols. Furthermore, any surgical mask such as a surgical N95 must be validated for fluid-resistant performance as regulated by the FDA. To this end, the methods discussed herein experimentally validated the system's virucidal capability, the impact on the filtration efficiency of N95 respirators, and the effect on the fluid resistance of the N95 respirators.

Validation of Ozone Concentration Produced by Generator

A Thermo 49C UV photometric ozone analyzer was connected to a sample ozone treatment chamber in order to assess the ozone concentration within the chamber. The rates of ozone production and decay in the test chamber were evaluated using this setup. The ozone generator's performance was quantified by measuring the maximum ozone generation rate of the ozone generator under continuous operation. This value was determined by measuring the concentration of ozone in this fixed-volume chamber over time. The decay rate of ozone at room temperature was determined by measuring the concentration of ozone in the chamber over time with the ozone generator turned off.

With the MQ-131 ozone concentration sensor 110 connected to the controller 26, an ozone setpoint of 25 ppm was set in the controller 26 programming after initial calibration against a metrology-grade ozone analyzer. The ozone concentration was then measured over the entire duration of a 150-minute typical treatment cycle. It was determined in this step that the sensitivity of the MQ-131 ozone sensor 110 was subject to change over time, so a calibration curve of the chamber concentration over time was plotted. In a future implementation of the controller 26 program, this calibration curve may be incorporated to ensure that the ozone level remains close to the setpoint within the chamber.

Validation of virucidal activity using P22 bacteriophage as a proxy for SARS-COV-2 Viral Preparation and Assay Bacteriophage P22 (ATCC® 19585-B1™) was propagated using *Salmonella typhimurium* (ATCC® 19585™) as the host bacterium using the double agar layer (DAL) technique. Briefly, 1 mL of the sample and 1 mL of the host cell bacteria, in the log-phase of growth, were added to a 5 mL of melted top agar in a test tube which was kept in a water bath at 48 degrees C. The mixture was gently poured onto a bottom agar plate and kept undisturbed to let the top agar to solidify. Then, the plate was incubated upside down at 37 degrees C. and plaques were counted after 24 hours of incubation. A positive and a negative control was included in every DAL assay.

The bottom agar plates were prepared using Tryptic Soy Agar (TSA) (provided by Difco Laboratories, Division of Becton Dickinson & Co. (i.e., Difco)). Prepared TSA was sterilized using an autoclave, cooled to 550 degrees C. and then dispensed into petri plates (20 ml per plate). Plated TSA was allowed to solidify and then stored at 4 degrees C. until used.

The top agar was prepared using Tryptic Soy Broth (TSB) (provided by Difco) by adding 0.7% agar (provided by Difco). Five mL of the top agar medium were dispensed to test tubes, capped and then autoclaved. The top agar tubes were stored at 4 degrees C. until used.

Inoculation and Test Procedure

A surgical 1860 N95 mask provided by 3M was cut to 2.5×2.5 cm pieces using a sterilized pair of scissors to obtain test coupons. Three coupons were placed in a sterilized petri dish, and each was inoculated with P22 bacteriophages at a total concentration of $1.6 \times 10^8$ PFUs per coupon by transferring 100 μL of the stock solution on their inner surface. The inner surface of the mask was selected based on its higher absorbance capability compared to the outer surface which is highly hydrophobic (data not shown). The inoculated coupons were allowed to dry at room temperature for 5 minutes to equilibrate with the mask material.

Triplicate sets of inoculated coupons were placed in the sterilization system 10 and were operated according to the parameters specified earlier.

After the operation cycle completed, test coupons were retrieved from the system 10. Each coupon was placed in a 50 mL tube containing 30 mL of elution buffer. The tube was vortexed to recover viruses from the coupon, and then the recovered buffer was analyzed using DAL technique.

Validation of N95 Respirator Filtration Efficiency Before and After Treatment

The capture efficiency tests were performed using a custom set-up. Challenge aerosols were generated using a medical nebulizer (drive medical, Port Washington, NY, USA) from aqueous solutions. Tests were performed using fumed silica nanoparticle slurry solutions which have been extensively characterized. The nebulization resulted in a broad challenge aerosol distribution and typical observational range was from 50-200 nm, a range which incorporates particles smaller than individual virions. This challenge aerosol covers the range of aerosols used in the NIOSH tests methods, 75±20 nm NaCl particles for N type masks and dioctyl phthalate (185±20 nm) particles for P99 masks. The challenge aerosol was passed through a trap bottle to remove larger particles. The aerosol then was measured directly or passed through a 25 mm diameter punch sample of the mask material, held in a filter cassette. The size resolved particle number concentration were determined with a Scanning Mobility Particle Sizer (SMPS) set-up consisting of a TSI 3088 Soft X-Ray neutralizer, a TSI 3082 aerosol classifier, a TSI 3085A Nano differential mobility analyzer (DMA) and a TSI 3752 high concentration condensation particle counter (CPC) (TSI, Shoreview, MN, USA). All tests were run in triplicate and for at least 10 minutes each. The respirators used for validation were surgical 3M 1860 N95s.

Validation of N95 Respirator Fluid Resistance Before and After Treatment

The fluid resistance of the N95 mask surface of control-group (untreated) and experimental-group (5 cycles of ozone treatment) N95 masks was quantified by means of a water drop deflection test. Distilled water was dropped from a fixed height of 17 cm above the base of the mask onto the surface of a mask. The mask was tilted such that the nose-clip edge of the mask was elevated 5 cm above the base of the mask. It was also qualitatively noted whether any absorption of the water drops into the mask surface was observable. The respirators used for validation were surgical 3M 1860 N95s.

Validation of Ozone Concentration Produced by Generator

Figure 16:
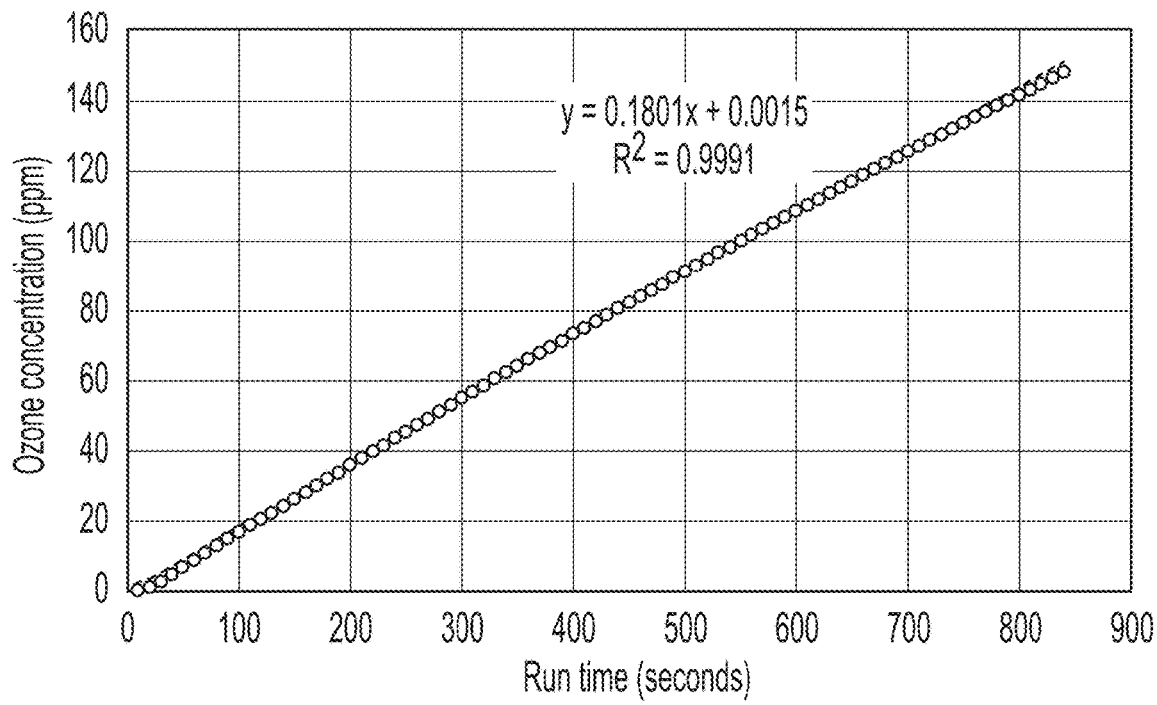
FIG. 16 illustrates an exemplary plot of ozone concentration over time in a 4-cubic foot chamber with the ozone generation systems of FIGS. 1-13 continuously operating.
Figure 17:
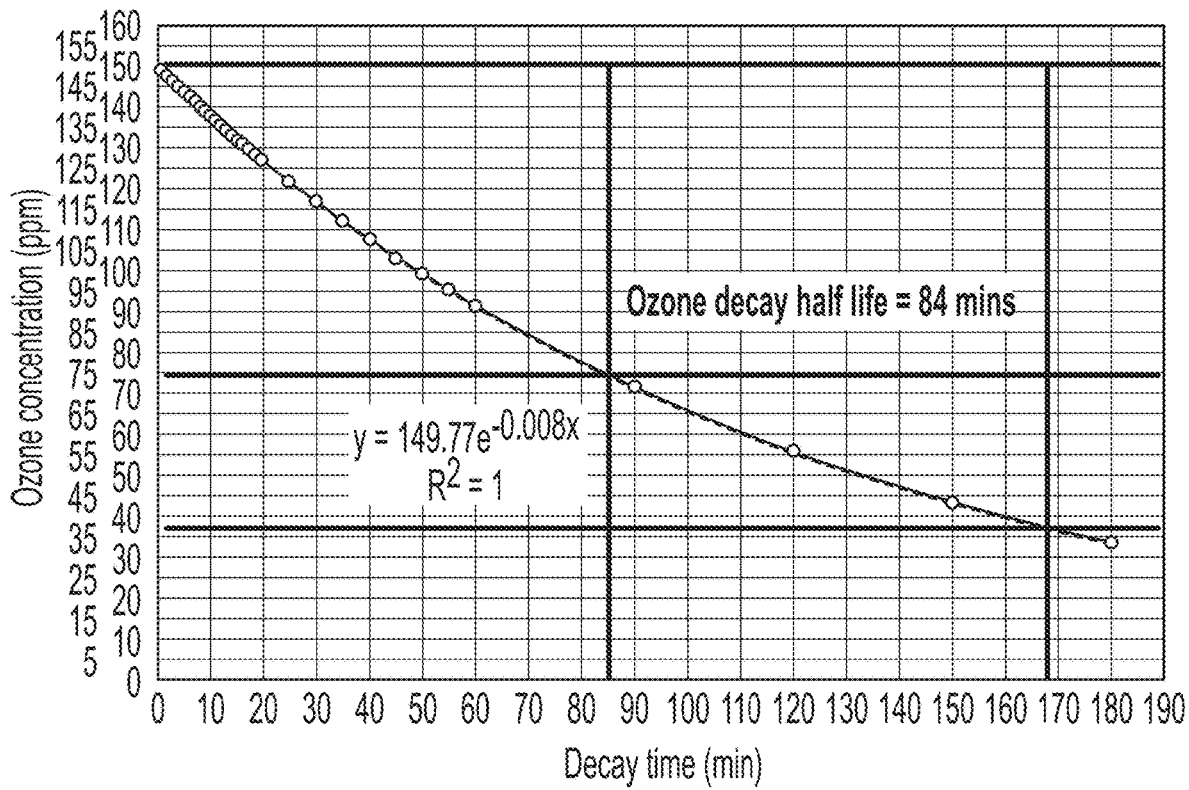
FIG. 17 illustrates an exemplary plot of ozone concentration over time in a 4-cubic foot chamber with the ozone generation systems of FIGS. 1-13 turned off (decay mode).

Initial testing with a prototype of the ozone generator yielded a production rate of 150 mg/hr, and ozone concentrations within the test chamber exceeding 150 ppm were achieved. A plot of ozone generation is shown in FIG. 16 and a plot of ozone decay is shown in FIG. 17 for the prototype ozone generator in a 4-cubic foot container as measured using the Thermo 49C.

Target concentrations for treatment range from 20 to 30 ppm. These results indicate that the ozone generator 14 will provide adequate ozone to the chamber to maintain this concentration range throughout the duration of the treatment cycle.

It is important to note that the material composition of items placed into the ozone treatment chamber or space may have a profound effect on the decay rate of the ozone concentration. Therefore, the addition of the MQ-131 ozone sensor to the system is desirable in order to control the ozone concentration within the chamber in a specified range, regardless of the ozone consumption rate of the items in the chamber.

The overall system 10, including the chamber 10, the complete ozone generator 14 system, and the MQ-131 ozone sensor 110, were operated for a typical treatment cycle period of 150 minutes. The ozone concentration within the chamber was measured every 10 minutes using the Thermo 49C, and the resulting concentration curve is shown in FIG. 18.

Figure 18:
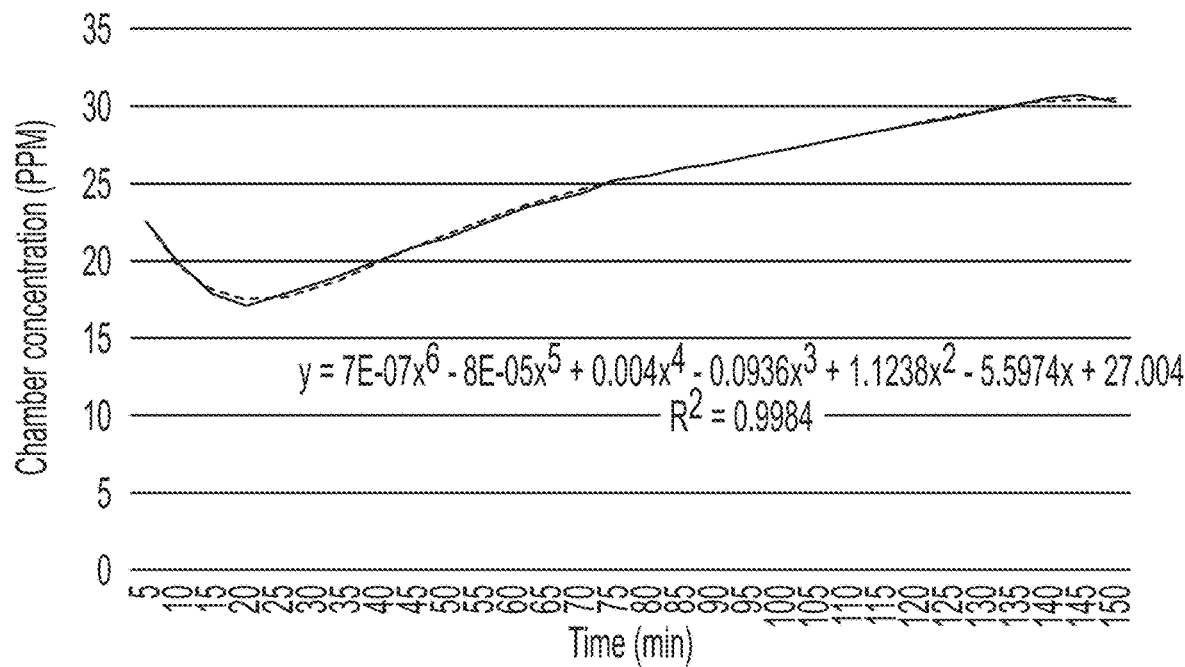
FIG. 18 illustrates an exemplary plot of ozone concentration over time under closed-loop control using a sensor of the ozone generation systems of FIGS. 11-13 and a setpoint of 25 ppm.

It is evident from the concentration curve of FIG. 18 that the sensitivity of the MQ-131 ozone sensor 110 drifts over time. Because the average chamber concentration is approximately equal to the set point of 25 ppm, the chamber may optionally be operated without software calibration. The chamber calibration curve may vary from one test run to the next, so calibration of the sensor using a precision ozone measurement system such as a Thermo 49C ozone analyzer is recommended if high ozone concentration precision is required.

Validation of Virucidal Activity Using P22 Bacteriophages as a Proxy for SARS-COV-2

The viral inactivation data is presented in Table 2. The ozone system achieves sterilization of viruses on N95 mask coupons. In all tests, greater than 6-log 10 reductions of P22 bacteriophage were achieved under the test conditions, which surpasses requirements for sterilization. The test coupons of inoculated N95 respirator material were exposed to an average ozone concentration of 25 ppm for 150 minutes, resulting in a total dose of 3750 ppm·min being administered to these samples. The observed 6-log 10 reduction of the viral proxy-a similar result to Yale University's validation of the BQ-50 VHP system (Bioquell, Horsham, PA) and NIOSH and CDC's evaluation of UVGI for sterilization of N95s—demonstrates the system's effectiveness against SARS-COV-2.

TABLE 2

Inactivation of P22 bacteriophages on N95 mask coupons using ozone.

| Treatment | Replicate | Initial $Log_{10}$ | Final $Log_{10}$ Recovered | $Log_{10}$ Reduction |
|---|---|---|---|---|
| Ozone | 1 | 8.2 | 1.78 | 6.43 |
|  | 2 | 8.2 | 1.78 | 6.43 |
|  | 3 | 8.2 | 1.48 | 6.73 |

Validation of N95 Respirator Filtration Efficiency Before and After Treatment

Figure 19:
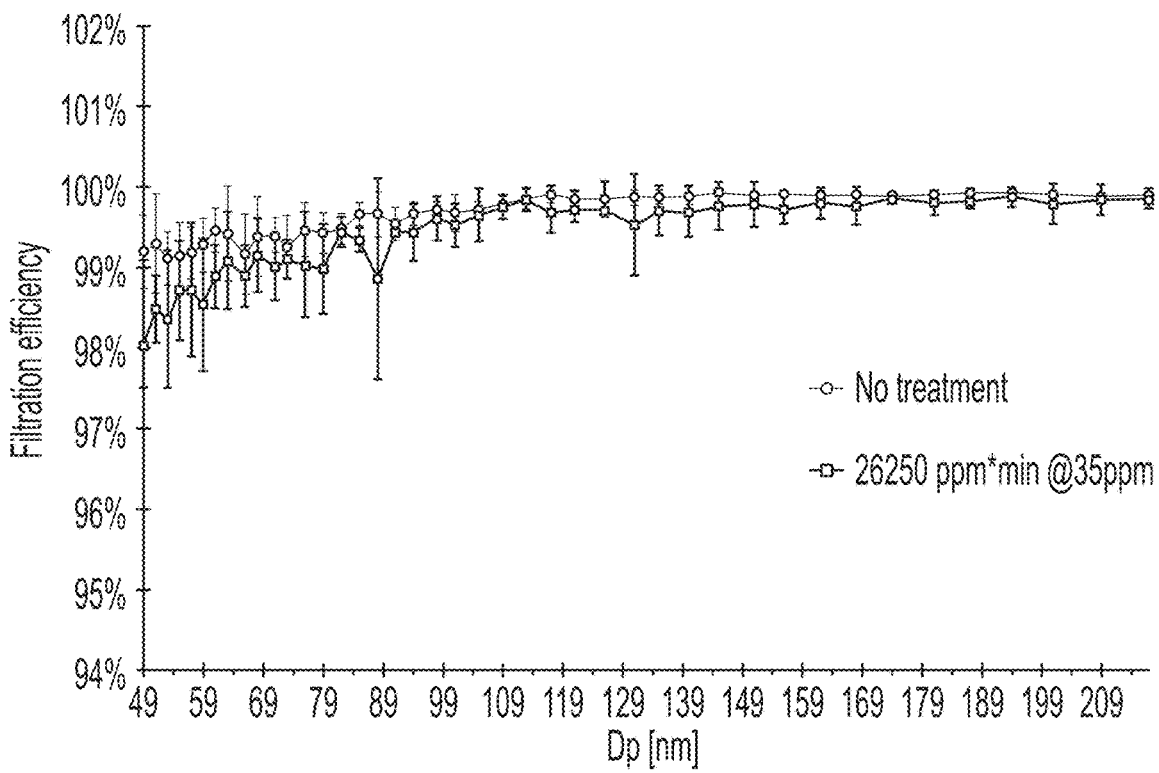
FIG. 19 illustrates exemplary filtration efficiency of untreated N95 respirators and N95 respirators treated with 26250 ppm·min ozone exposure.

The filtration validation study described in the methods section indicated that at the challenge aerosol sizes tested, the measured capture efficiency of one sample respirator treated with 5 ozone treatment cycles under the procedures recommended herein remained above the minimum filtration efficiency value of 95% required for the respirators to be classified as N95 type (the NIOSH validation test uses similar particles but different operating conditions). The worst-case value of measured filtration efficiency for a 5-cycle treated N95 respirator was found to be 98%. These results indicate a minor reduction in filtration efficiency at lower particulate sizes after several cycles through the recommended ozone treatment process, but they are indicative that the minimum filtration efficiency required for N95 respirator classification is most likely to be preserved over a wide range of particulate sizes even beyond five treatment cycles. The results of this filtration efficiency testing are depicted in FIG. 19.

Validation of N95 Respirator Fluid Resistance Before and After Treatment

Initial testing of N95 surgical masks that have been treated with three and five cycles of ozone treatment showed degradation of the hydrophobic layer on the surface of the mask, although this degradation may be mitigated as discussed below.

Supplementary Qualitative Materials Testing Methods

In order to assess the effects of ozone exposure on certain types of shoe, fabric material, and shoe covering, an ozonation chamber was prepared using one of the Luminosity Lab low-cost modular ozone generator units. A 22.7-liter cooler was used as the sealed chamber, and ozone concentration was determined by interpolation of prior characterization curves.

The ozone generator was initially configured for a 16.6% duty cycle, allowing 10 seconds of ozone generation time for every 50 seconds of ozone decay time. This value was selected before the decay dynamics of the ozone chamber were well-understood, and may be considered arbitrary. This duty cycle preserves the approximately linear ozone concentration rise, as it is still within an order of magnitude of the continuous-operation regime. The shoes and material samples to be tested included the following: 1 US Polo Assn "Converse"-style shoe, model number 21629601A, 1 Adidas "Ultra Boost" running shoe, model number 606001, 1 Saucony "Cohesion 10" running shoe, model number S25354-1, 1 Reef Flip-Flop, unknown composition, no model number available, 1 confirmed EVA foam flip, no model number available, 2 elastic shoe coverings, different manufacturers, 1 cloth sample, 100% nylon on one side and 100% polyester on the other side, 1 latex balloon.

The test chamber was operated for 1 hour per test cycle to allow sufficient time for ozone concentration to rise and ozone to diffuse into the materials under test. The final ozone concentration can be computed according to the previous linear approximation as follows:

$$C_{O3Final}=0.1488t(3600)=535.8 \text{ ppm}$$

Under the linear approximation of ozone concentration rise, the average ozone concentration throughout the treatment process can be computed as follows:

$$C_{O3Average}=(C_{O3Final}-C_{O3initial})/2$$

$$C_{O3Average}=(535.8 \text{ ppm}-0 \text{ ppm})/2=267.9 \text{ ppm}$$

The total approximate dose (in ppm·min) to which the test items were exposed is therefore:

$$Dose_{O3}=C_{O3Average}*t=267.9 \text{ ppm}*60 \text{ min}=16071 \text{ ppm·min}$$

Supplementary Qualitative Materials Testing Observations

Both visual inspection and functionality inspection did not show any signs of degradation on any of the shoe samples tested after exposure to 16071 ppm·min of ozone. This is indicative that the materials from which these shoes are composed are likely not heavily affected by ozone in the dosages that would be commonly applied for sterilization purposes.

The elastic shoe cover from one of the manufacturers (darker blue) showed marked signs of degradation of the elastic after the 16071 ppm·min ozone exposure test. The elastic shoe cover from the other manufacturer did not show evidence of elastic degradation during the treatment period. The non-elastic fabric material did not show signs of degradation.

The nylon and polyester fabric materials did not show signs of degradation after the 16071 ppm·min ozone exposure.

The latex balloon showed extreme deterioration after the 16071 ppm·min ozone exposure. A crack formed in the material and was easily expanded by stretching. The latex took on a sticky consistency and a strong burnt odor.

Ozone Release Testing in Typical Occupied Space

In order to establish the effect of operating the ozone sterilization system in a room with limited ventilation, an experiment was carried out in which the ozone sterilization system was placed into a room with no direct ventilation alongside a Thermo 49C ozone measuring system. The test was intended to determine if, under typical worst-case usage conditions, the operation of the ozone sterilization system raises ambient concentrations of ozone in an occupied space to levels exceeding the OSHA permissible exposure limit (PEL) of 300 parts per billion (PPB) over a 15-minute window.

Testing was performed in a 2.7-meter by 2.1-meter room with a 0.61-meter by 0.61-meter cabinet in one corner. The ceiling height of the room was 2.4 meters. The approximate total volume of the room was 12.7 cubic meters. Special care was taken to ensure that the building HVAC system was disabled throughout each period of testing, and that all exhaust fans in the area were turned off, windows were closed, and no sources of draft were present. The Thermo 49C intake hose was positioned near the center of the room approximately 1 meter from the floor during room sampling.

The Thermo 49C ozone analyzer was first connected to power and allowed to warm up. A background level of ozone was measured in the room prior to each testing round. The ozone sterilization system was then powered and allowed to operate until the Thermo 49C ozone analyzer indicated it had reached an internal ozone concentration of 30,000 PPB (30 ppm) as measured from the sampling port on the treatment chamber. The intake of the Thermo 49C was then moved to the room air sampling location, the power was disconnected from the ozone generator, and the lid was removed. The experimenter promptly left the room and closed the door, allowing the room to stand for 15 minutes to allow ozone gas to diffuse evenly throughout the room. After 15 minutes, the door was opened and the most recent ozone concentration measured by the Thermo 49C ozone analyzer was recorded.

This experiment was repeated three times. The building HVAC system was operated after each test to remove most of the ozone from the room. To account for changes in the background level of ozone in the testing room due to previous tests, the difference between the initial and final ozone levels in each test was tabulated. The results of each of these tests can be found in Table 2, below.

TABLE 3

Results of 20-minute room ozone concentration after each ozone release test.

| Test Number | Background Ozone Level (PPB) | Post-Treatment Ozone Level (PPB) | Change in Ozone Level (PPB) |
| --- | --- | --- | --- |
| Test 1 | 12.7 | 31.5 | 18.8 |
| Test 2 | 13.0 | 31.1 | 18.1 |
| Test 3 | 13.3 | 28.3 | 15.0 |

Because the ozone level within the test room never exceeded the OSHA PEL of 300 PPB over a 15-minute window (and remained approximately 10 times lower than this limit), it is likely that the operation of the system is safe indoors under typical operating conditions. It is still recommended that the system be operated in a well-ventilated area, and that the user avoid directly inhaling the exhaust gases released during opening of the container.

DISCUSSION

Sterilization of healthcare-related items is commonly achieved through the use of gas-phase disinfectants such as ethylene oxide (EtO), nitrogen dioxide, peracetic acid, ortho-phthalaldehyde (OPA), and glutaraldehyde (Cidex). To this end, many common methods used for decontamination of a variety of items in hospitals and other sterile environments require an existing feedstock of a sterilization agent. In contrast, the sterilization systems 10 discussed herein require no existing feedstock to produce the sterilization agent and only needs a power supply to operate continuously. This generates significantly fewer waste materials produced in comparison to orthodox clinical high-throughput sterilization procedures. Similarly, using the ozone system over common clinical decontamination methods also significantly reduces the resource costs associated with decontamination and sterilization. Moreover, many of the aforementioned sterilization agents require a relatively long treatment time. For example, commonly used gas-phase EtO requires a treatment time of over 12 hours. In contrast, this ozone system was shown to sterilize P22-inoculated N95 respirators in 1 hour, suggesting that the system is also more time efficient in sterilization. As such, the ozone system described in this paper may provide first responders, businesses, educational institutions, and healthcare facilities with unprecedented access to easy-to-use, affordable sterilization technology.

To verify the performance of this device, the system's virucidal efficacy, impact on the filtration efficiency of N95 respirators, and compatibility with fluid-resistant N95 respirators were analyzed experimentally. Measurements taken from a sample ozone treatment chamber using a Thermo 49C ozone analyzer indicated that under closed-loop control for one treatment cycle, a concentration of ozone ranging from 20-32 ppm is maintained with the proposed system design after an initial warm-up period of 45 minutes. In a biological validation test in which P22 bacteriophage was utilized as a surrogate for SARS-COV-2, an exposure time of 150 minutes at 25±5 ppm ozone concentration was shown to provide greater than 6-$\log_{10}$ reduction in viral load, similar to Yale University's methodology for validating the Bioquell sterilization system for use during the COVID-19 epidemic. This result not only meets but exceeds the ASTM definition for sterilization.

Furthermore, N95 respirators treated with 5 cycles of 150-minute exposure at 25±5 ppm ozone concentration remained above the minimum required filtration efficiency of 95% for this type of respirator, indicating that ozone does not pose a significant risk to filtration efficiency in the concentrations, time, and number of cycles studied.

Conversely, the ozone CT tested did have an effect on the outer hydrophobic coating of surgical N95 respirators, which showed loss of fluid resistance in a water droplet test after less than 3 cycles of ozone treatment. Similarly, polyisoprene elastic bands showed visible degradation after exposure to multiple sterilization cycles. These negative effects may be circumvented, however, by applying a replacement hydrophobic layer, (e.g., Scotchgard™ Fabric Protector, 3M Company—Cat. No. 4101, 4106) after each sterilization cycle and coating elastic straps in an ozone-resistant substance during treatment (e.g., mineral oil or petrolatum).

The sterilization and filtration results suggest that this system is well-suited for processing most face coverings currently available to the general public. Additionally, the system may be suitable for use with many hard materials typically found in household and commercial settings, such as tools, office supplies, electronic devices, clothing, and other frequently-handled items. In particular, items consisting of stainless steel, aluminum, PVC, nylon, teflon, silicone, plexiglass, borosilicate glass have been shown to be compatible with ozone sterilization processes.

Another consideration is the potential impact of ozone gas on human health. For safety, OSHA requires ozone gas exposure to remain below. 1 ppm over an 8-hour, time-weighted average. We have shown that in a typical occupied space with limited ventilation, ozone concentrations 15 minutes after each treatment cycle remain much lower than maximum the OSHA permissible exposure limit (PEL), indicating the safety of the described system 10. Nevertheless, after a treatment cycle, one should turn their head away from the system when opening the chamber, allow the gas to disperse for 10 minutes to 15 minutes before removing any items, and only open the system in a well-ventilated space.

CONCLUSIONS

Achieving a 6-$\log_{10}$ reduction in P22 bacteriophage viral loads suggests that our ozone system will be effective in eliminating SARS-COV-2 on various items including PPE. Furthermore, decontaminated N95 respirators still consistently exceeded standard filtration performance as required by NIOSH standards. While the potential degradation of the elastic straps and fluid resistant layer of N95 respirators requires additional considerations (and mitigation techniques), the 6-$\log_{10}$ reduction of viral loads and minimal effect on filtration performance demonstrates that the ozone system 10 can serve as a cost-effective sterilization tool for certain applications. Such applications include the sterilization of masks (e.g., non-hydrophobic masks) or other face coverings, as well as potentially-contaminated items worn in medical environments such as hospital gowns and shoes. Moreover, given the efficacy of the tested system against P22 bacteriophage loads, ozone can be used to sterilize other compatible items outside of the clinic. For example, businesses operating during the COVID-19 pandemic can use our ozone sterilization system to sterilize face coverings for reuse, thus reducing the financial burden of purchasing new face coverings and inspiring both employee and consumer confidence. With growing demand for surgical masks and other face coverings due to community use, widespread ozone sterilization can also serve as a tool to reduce the impact of this newfound demand on the personal protective equipment supply chain.

Beyond the COVID-19 epidemic, the ozone generator 14 offers a cost-effective solution to the environmental toll endured from the widespread use of waste-generating decontamination agents. Present decontamination agents present significant monetary costs and result in the generation of large quantities of biohazard and chemical waste. In contrast, the ozone system 10 requires no initial chemical feedstock and does not generate any significant biohazard waste. Furthermore, the system's 10 lack of feedstock allows it to be used wherever power is available. This, combined with the system's 10 use of affordable parts from outside medical supply chains, makes it a scalable solution even during and after the ongoing pandemic.

Large-scale adoption of the ozone system 10, where appropriate, can allow users to effectively decontaminate materials while also conserving capital dedicated to sterilization supplies and reducing the environmental footprint left behind from high-throughput decontamination.

Various features and advantages are set forth in the following claims.

What is claimed is:

1. A sterilization system comprising:
   a chassis;
   a controller;
   a transformer positioned within the chassis and including a primary side and a secondary side, the primary side in communication with the controller;
   an ozone generator positioned within the chassis and in communication with the secondary side of the transformer and the controller, the ozone generator includes a first electrode and a second electrode twisted together with a twist density to provide 0.5 mm to 2 mm of airspace between the first electrode and the second electrode, the twisted first and second electrodes being configured in a coiled arrangement; and
   a power source positioned within the chassis and in communication with the controller and the primary side of the transformer,
   wherein the ozone generator ionizes atmospheric oxygen through an application of corona discharge, and
   wherein each of the first and second electrodes are formed of wire insulated in silicone-rubber.

2. The sterilization system of claim 1, wherein the transformer is an ignition coil.

3. The sterilization system of claim 1, wherein a fan is positioned within the chassis.

4. The sterilization system of claim 1, wherein the first electrode is coupled to the secondary side of the transformer and the second electrode is coupled to the controller.

5. The sterilization system of claim 4, further comprising a transistor positioned between (i) the controller and (ii) the primary side of the transformer, wherein the controller is configured to turn the transistor to turn the transistor on and off using a pulse-width modulation signal.

6. A sterilization system comprising:
   a controller positioned within a chassis defining a sterilization chamber;
   an ignition coil positioned within the sterilization chamber and including a primary side and a secondary side, the primary side in communication with the controller;
   a first electrode and a second electrode twisted together with a twist density to provide 0.5 mm to 2 mm of airspace between the first electrode and the second electrode, the twisted first and second electrodes being configured in a coil coiled arrangement, the coil of the first and the second electrodes positioned within the sterilization chamber and in communication with the secondary side of the ignition coil and the controller;
   a power source positioned in the sterilization chamber and communication with the controller and the primary side of the ignition coil; and
   a fan in communication with the controller, the fan configured to circulate air across the coil of the first electrode and the second electrode,
   wherein the first and second electrodes ionize atmospheric oxygen through an application of corona discharge, and wherein each of the first and the second electrodes are formed of wire insulated in silicone-rubber.

7. The sterilization system of claim 6, further comprising a chassis, wherein the ignition coil, the twisted first and the second electrodes, the power source, and the fan are positioned within the chassis.

8. The sterilization system of claim 7, wherein the chassis includes a body having the sterilization chamber and a lid removably secured to the body to close the sterilization chamber, the sterilization chamber configured to receive materials to be sterilized.

9. The sterilization system of claim 8, wherein the sterilization chamber contains one or more ozone level sensors for measuring the level of ozone present inside of the sterilization chamber.

10. The sterilization system of claim 9, wherein the one or more ozone level sensors provide feedback to the controller such that the controller adjusts ozone production output to maintain a pre-determined level of ozone within the sterilization chamber.

11. The sterilization system of claim 10, wherein the controller includes a timer configured to measure a pre-determined amount of time, the controller configured to expose the materials within the sterilization chamber to the pre-determined level of ozone for a pre-determined amount of time.

12. The sterilization system of claim 6, wherein the first electrode is coupled to the secondary side of the ignition coil and the second electrode is coupled to the controller.

13. The sterilization system of claim 12, further comprising a transistor positioned between (i) the controller and the (ii) primary side of the ignition coil, wherein the controller is configured to turn the transistor to turn the transistor on and off using a pulse-width modulation signal.

14. A method of assembling a sterilization system, the method comprising:
   forming an ozone generator by twisting a first electrode with a second electrode and creating an airspace of 0.5 mm to 2.0 mm therebetween;
   forming a coil with the twisted first electrode and the second electrode;
   coupling a controller to a primary side of a transformer; and
   coupling the ozone generator to a secondary side of the transformer;
   wherein a power source is coupled to (i) the primary side of the transformer and (ii) the controller.

15. The method of claim 14, further comprising positioning the ozone generator and power source into a chassis.

16. The method of claim 14, wherein the first electrode is coupled to the secondary side of the transformer and the second electrode is coupled to the controller.

17. The method of claim 16, wherein a transistor is positioned between (i) the controller and (ii) the primary side of the transformer, wherein the controller is configured to turn the transistor to turn the transistor on and off using a pulse-width modulation signal.

* * * * *